United States Patent [19]

Ciganek

[11] Patent Number: 5,216,018
[45] Date of Patent: Jun. 1, 1993

[54] HYDROISOINDOLINES AND HYDROISOQUINOLINES AS PSYCHOTROPIC

[75] Inventor: Engelbert Ciganek, Kennett Square, Pa.

[73] Assignee: Du Pont Merck Pharmaceutical Company, Wilmington, Del.

[21] Appl. No.: 836,229

[22] Filed: Feb. 14, 1992

[51] Int. Cl.$^5$ .................. A61K 31/40; C07D 209/04
[52] U.S. Cl. ................................ 514/416; 548/468
[58] Field of Search .................. 548/470; 514/416

[56] References Cited

FOREIGN PATENT DOCUMENTS 3614906 11/1987 Fed. Rep. of Germany ...... 548/469
3721723 12/1989 Fed. Rep. of Germany ...... 546/112

OTHER PUBLICATIONS

Bartman et al., Synth. Commun. 1988, 18:711.
Gray et al., J. Am. Chem. Soc. 1962, 84:89.
Otzenberger et al., J. Org. Chem. 1974, 39:319.
Rehse et al., Arch. Pharm. 1979, 312:982.
Dunet et al., Bull. Soc. Chim. France. 1956, 154:906.
Pogossyan et al., Arm. Khim. Zh. 1980, 33:157.
Rashidyan et al., Arm. Khim. Zh. 1970, 23:474.
Pogossyan et al., Arm. Khim. Zh. 1979, 32:151.
Rashidyan et al., Arm. Khim. Zh. 1968, 21:793.
Grieco et al., J. Chem. Soc. 1987, p. 185.
Larsen et al., J. Am. Chem. Soc. 1986, 108:3512.
Archer et al., J. Med. Chem. 1987, 30:1204.
Deslongchamps et al., Can. J. Chem. 1975, 53:3613.
Jirkovsky et al., Coll. Czech. Chem. Commun. 1964, 29:400.
Meyers et al., J. Org. Chem. 1986, 51:872.

Primary Examiner—Mary Lee
Assistant Examiner—Joseph K. McKane
Attorney, Agent, or Firm—Gerald J. Boudreaux

[57] ABSTRACT

There are provided nitrogen-containing bicyclic compounds which are useful in the treatment of physiological or drug induced psychosis or dyskinesia in a mammal. These novel compounds are selective sigma receptor antagonists and have a low potential for movement disorder side effects associated with typical antipsychotic agents.

26 Claims, No Drawings

HYDROISOINDOLINES AND HYDROISOQUINOLINES AS PSYCHOTROPIC

FIELD OF THE INVENTION

This invention relates to novel nitrogen-containing bicyclic compounds, pharmaceutical compositions containing these compounds and methods of using these compounds to treat physiological or drug induced psychosis and as antidyskinetic agents.

BACKGROUND OF THE INVENTION

Gray et al. in J. Am. Chem. Soc., 84, 89 (1962) and U.S. Pat. No. 3,127,413 disclose octahydroisoindoles of the formula:

Ar—Alk—N⟨...⟩OR, OR'

The octahydroisoindoles are useful as tranquilizing agents and for potentiating the action of barbiturates.

Processes for preparing trisubstituted perhydro isoindolines of the following formula are described by Achini et al, Helvetica Chimica Acta, 57, 572 (1974):

HO, H, NCH$_2$Ph, H

Otzenberger et al., J. Org. Chem., 39, 319 (1974) disclose a compound of formula:

NCH$_2$Ph

No utility is disclosed.

Rehse et al., Arch. Pharm. (Weinheim), 312, 982 (1979), disclose a compound of formula:

Ph, N, OCH$_3$, OCH$_3$

The authors disclose this compound is a dopamine agonist.

German Patent DE 3614906 discloses a compound of formula:

N, CH$_3$, t-butyl

The patentee discloses this compound is a plant fungicide.

Dunet et al., Bull Soc. Chim. France, 1956, 906, disclose a compound of formula:

N

The authors do not disclose a utility for this compound.

Pogossyan et al., Arm. Khim. Zh., 33, 157 (1980), disclose compounds having the formula:

NH$_2$, R, N, N, H

The authors disclose these compounds are reserpine antagonists.

Rashidyan et al., Arm. Khim. Zh., 23, 474 (1970), disclose compounds of formula:

R$^2$, R$^1$, NCH$_2$Ph

The authors do not disclose a utility for these compounds.

Pogossyan et al., Arm. Khim. Zh., 32, 151 (1979), disclose a compound of formula:

N, N, H

The authors do not disclose a utility for this compound.

Rashidyan et al., Arm. Khim. Zh., 21, 793 (1968), disclose a compound having the formula:

Cl, NCH$_2$Ph

The authors do not disclose a utility for this compound.

Grieco et al., J. Chem. Soc., Chem. Soc., 1987, 185, disclose a compound of formula:

CH$_2$, NCH$_2$Ph

The authors do not disclose a utility for this compound.

Larsen et al., J. Am. Chem. Soc., 108, 3512 (1986), disclose a compound having the formula:

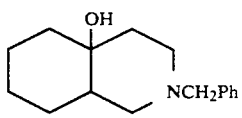

The authors do not disclose a utility for this compound.

German Patent 3721723 (Hoechst AG) describes substituted 6-oxo-decahydroisoquinolines of the formula:

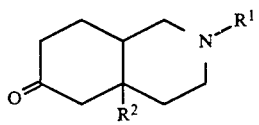

These compounds are useful as antihypertensives and sedatives.

Archer et al., J. Med. Chem., 30, 1204 (1987), disclose a compound having the formula:

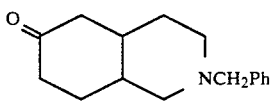

The authors do not disclose a utility for this compound.

Deslongchamps et al., Can. J. Chem., 53, 3613 (1975), disclose a compound having the formula:

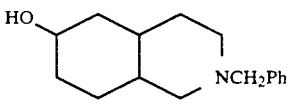

The authors do not disclose a utility for this compound.

Jirkovsky et al., Coll. Czech. Chem. Commun., 29, 400 (1964), disclose a compound having the formula:

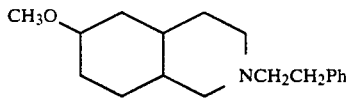

The authors do not disclose a utility for this compound.

Meyers et al., J. Org. Chem., 51, 872 (1986), disclose a compound of formula:

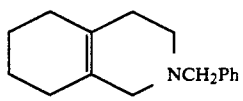

The authors do not disclose a utility for this compound.

Bartmann et al., Synth. Commun., 18, 711 (1988), disclose compounds of formula:

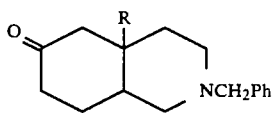

The authors do not disclose a utility for these compounds.

Compounds of the present invention demonstrate sigma receptor affinity. It is this sigma receptor affinity of the compounds of the present invention which makes them so advantageous over the compounds in the prior art. Traditionally, antipsychotic agents have been potent dopamine receptor antagonists. For example, phenothiazines such as chlorpromazine and most butyrophenones such as haloperidol are potent dopamine receptor antagonists. These dopamine receptor antagonists are associated with a high incidence of side effects, particularly Parkinson-like motor effects or extra-pyramidal side-effects (EPS), and dyskinesias including tardive dyskinesias at high doses. Many of these side effects are not reversible even after the dopamine receptor antagonist agent is discontinued.

The present invention is related to antipsychotic agents which are sigma receptor antagonists, not traditional dopamine receptor blockers known in the art, and therefore the compounds of the present invention have low potential for the typical movement disorder side-effects associated with the traditional dopamine antagonist antipsychotic agents while they maintain the ability to antagonize aggressive behavior and antagonize hallucinogenic-induced behavior.

SUMMARY OF THE INVENTION

Compounds of this invention are novel antagonists of sigma receptors, which may be useful for the treatment of physiological and drug-induced psychosis and dyskinesia.

The compounds of the present invention are nitrogen-containing bicyclic compounds having the formula:

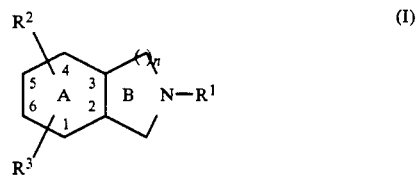

or a pharmaceutically acceptable salt, N-oxide, chiral, enantiomeric, diastereomeric or racemic form thereof, wherein:

$n = 1$ or 2;

$R^1$ is selected from the group including:
$C_1$-$C_8$ alkyl substituted with 1 or more $R^4$,
$C_3$-$C_8$ cycloalkyl, and $C_4$-$C_{10}$ cycloalkyl-alkyl;

$R^2$ and $R^3$ are optional and may be independently selected from the group including:
$C_1$-$C_8$ alkyl substituted with 0-3 $R^4$, $C_2$-$C_8$ alkenyl, $C_3$-$C_8$ cycloalkyl, $C_4$-$C_{10}$ cycloalkyl-alkyl
$C_1$-$C_6$ perfluoroalkyl, aryl optionally substituted with 1-3 of the following:
$C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN, except that $R^2$ and/or $R^3$ when aryl may not be at the 2- or 3-position, a heterocyclic ring system selected from the group including furyl, thienyl, pyrrolyl, pyridyl, indolyl, quinolyl, isoquinolyl, benzofuryl, benzothienyl, pyrimidyl, pyrazinyl, quinazolyl, phthalazinyl, naphthyridinyl,
—F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, COR$^7$, —CN, =O, forming a carbonyl group, or $R^2$ and $R^3$ may be taken together to form a ring comprising: $-CHR^6-CHR^6-CHR^6-$, $-CHR^6-CHR^6-CHR^6-$, $-CHR^6-CR^6=CR^6-$, $-CHR^6-CHR^6-CHR^6-CR^6=$, $-CHR^6-CHR^6-CR^6=CR^6-$, $-CHR^6-CR^6=CHR^6-CHR^6-$, $-CR^6=CHR^6-CHR^6-CR^6=$, $-CR^6=CHR^6-CR^6=CR^6-$, and $-CHR^6-CR^6=CHR^6-CR^6=$;

$R^4$ may be aryl optionally substituted with 1-3 of the following:

$C_1$-$C_8$ alkyl, $C_2$-$C_8$ alkenyl, $C_3$-$C_8$ cycloalkyl, $C_1$-$C_6$ perfluoroalkyl, aryl, $-F$, $-Cl$, $-Br$, $-I$, $-NO_2$, $-OR^5$, $-OC(=O)R^7$, $-N(R^7)_2$, $-SR^5$, $-S(O)R^5$, $-SO_2R^5$, $-CO_2R^7$, $-CN$, or $R^4$ may be a heterocyclic ring system selected from the group including:

furyl, thienyl, pyrrolyl, pyridyl, indolyl, quinolyl, isoquinolyl, benzofuryl, benzothienyl, pyrimidyl, pyrazinyl, quinazolyl, phthalazinyl, naphthyridinyl;

$R^5$ is independently selected at each occeurrence from the group including:

hydrogen, $C_1$-$C_{14}$ alkyl, $C_3$-$C_8$ cycloalkyl, $C_1$-$C_6$ alkanoyl, and aryl;

$R^6$ is independently selected at each occurrence from the group including:

hydrogen, phenyl, benzyl, phenethyl, phenoxy, benzyloxy, halogen, hydroxy, nitro, cyano, $C_1$-$C_5$ alkyl, $C_3$-$C_{10}$ cycloalkyl, $C_3$-$C_6$ cycloalkylmethyl, $C_7$-$C_{10}$ arylalkyl, $C_1$-$C_4$ alkoxy, $-NR^7R^8$, $C_2$-$C_6$ alkoxyalkyl, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, $-SO_2R^7$, $-S(=O)R^7$, $-SO_2NR^7R^8$, $-SO_3H$, $-CF_3$, $-OR^7$, $-CHO$, $-CH_2OR^7$, $-CO_2R^7$, $-C(=O)R^7$, $-NHSO_2R^8$, $-OCH_2CO_2H$, or a 5- or 6-membered heterocyclic ring containing from 1 to 4 heteroatoms selected from oxygen, nitrogen or sulfur;

$R^7$ is H, phenyl, benzyl or $C_1$-$C_6$ alkyl;

$R^8$ is H or $C_1$-$C_4$ alkyl;

or $R^7R^8$ can join to form $-(CH_2)_4-$, $-(CH_2)_5-$, $-(CH_2CH_2N(R^9)CH_2CH_2)-$, or $-(CH_2CH_2OCH_2CH_2)-$;

$R^9$ is H or $CH_3$; and the A ring may contain one double bond;

with the following provisos:

(1) when $R^2$ and $R^3$ are on the same atom, neither $R^2$ nor $R^3$ can be OH;

(2) when n=1 and $R^2$ is 5-hydroxy and $R^3$ is 6-alkoxy and the A ring contains no double bond, then $R^1$ cannot be $-CH_2CH_2Ph$ or $-CH_2CH_2(3\text{-indolyl})$ or $-CH_2CH_2(\text{naphthyl})$;

(3) when n=1 and $R^2$ is 5-hydroxy or 5-acyloxy and $R^3$ is alkoxy and the A ring contains no double bond, then $R^1$ cannot be $-(CH_2)_p\text{aryl}$ or $-(CH_2)_p\text{heteroaryl}$ wherein p=1-3 and the aryl or heteroaryl groups are substituted with 1-3 $R^7$;

(4) when N=1 and $R^2$ is not present and $R^3$ is not present and the A ring contains a double bond between carbons 5 and 6, then $R^1$ cannot be $-CH_2Ph$;

(5) when n=1 and $R^2$ is 5-Cl and $R^3$ is not present and the A ring contains a double bond between carbons 5 and 6, then $R^1$ cannot be $-CH_2Ph$;

(6) when n=1 and $R^2$ is 5-OH and $R^3$ is not present and the A ring contains no double bond, then $R^1$ cannot be $-CH_2Ph$;

(7) n=1 and $R^2$ is 5-keto or 5-[1-(1,3-dioxolane)] and $R^3$ is not present and the A ring contains no double bond, then $R^1$ cannot be $-CH_2Ph$;

(8) when n=1 and $R^2$ is not present and $R^3$ is not present and the A ring contains no double bond, then $R^1$ cannot be $-CH_2(2\text{-methylcyclohexyl})$;

(9) when n=1 and $R^2$ is 5-Ph and $R^3$ is not present and the A ring contains no double bond, then $R^1$ cannot be $-CH_2CH_2(3,4\text{-dimethoxyphenyl})$;

(10) when n=1 and $R^2$ is not present and $R^3$ is not present and the A ring has a double bond between the 5 and 6 carbons, then $R^1$ cannot be $-CH_2CH_2(3\text{-indolyl})$;

(11) when n=1 and $R^2$ is 5-NH2 and $R^3$ is not present and the A ring contains no double bond, then $R^1$ cannot be $-CH_2CH_2(3\text{-indolyl})$ or $CHMeCH_2(3\text{-indolyl})$;

(12) when n=1 and $R^2$ is not present and $R^3$ is not present and the A ring contains no double bond, then $R^1$ cannot be $-CH_2CHCH_3CH_2(4\text{-t-butylphenyl})$;

(13) when n=2 and $R^2$ is 3-OH or 5-OH or 5-(=O) and $R^3$ is not present and the A ring contains no double bond, then $R^1$ cannot be $-CH_2Ph$;

(14) when n=2 and $R^2$ is 3-alkyl optionally substituted with cycloalkyl, alkenyl or aryl groups, 3-alkenyl, 3-cycloalkyl, 3-cycloalkenyl, 3-fluorenyl, 3-CHCNPh, 3-CHNO2Ph, or 3-CH(CO2R^5)_2, and $R^3$ is 5-(=O) and the A ring has no double bond, then $R^1$ cannot be $-(CH_2)_q\text{aryl}$ wherein q=1-4;

(15) when n=2 and $R^2$ is 5-(=O) and $R^3$ is not present and the A ring contains a double bond between 3 and 4 carbons, then $R^1$ cannot be $CH_2Ph$;

(16) when n=2 and $R^2$ is not present and $R^3$ is not present and the A ring contains a double bond between the 2 and 3 carbons, then $R^1$ cannot be $CH_2Ph$;

(17) when n=2 and $R^2$ is 5-(=CH_2) or 5-(=O) and $R^3$ is not present and the A ring contains no double bond, then $R^1$ cannot be $-CH_2CH_2-3-(N-\text{phenylsulfonyl})\text{indoyl}$; and

(18) when n=2 and $R^2$ is 6-OMe and $R^3$ is not present and the A ring contains no double bonds, then $R^1$ cannot be $CH_2CH_2Ph$.

Also provided by the present invention is a method for treatment of physiological or drug induced psychosis or dyskinesia in a mammal comprising administering to a mammal in need of such treatment an antipsychotic or antidyskinetic effective amount of a compound of formula:

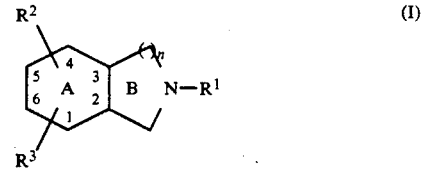

or a pharmaceutically acceptable salt, N-oxide, chiral, enantiomeric, diastereomeric or racemic form thereof, wherein:

n=1 or 2;

$R^1$ is selected from the group including:

$C_1$-$C_6$ alkyl substituted with 1 or more $R^4$, $C_3$-$C_8$ cycloalkyl, and $C_4$-$C_{10}$ cycloalkyl-alkyl;

$R^2$ and $R^3$ are optional and may be independently selected from the group including:

$C_1$-$C_8$ alkyl substituted with 0-3 $R^4$, $C_2$-$C_8$ alkenyl, $C_3$-$C_8$ cycloalkyl, $C_4$-$C_{10}$ cycloalkyl-alkyl $C_1$-$C_6$ perfluoroalkyl, aryl optionally substituted with 1-3 of the following:

$C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN, except that R$^2$ and/or R$^3$ when aryl may not be at the 2- or 3-position, a heterocyclic ring system selected from the group including furyl, thienyl, pyrrolyl, pyridyl, indolyl, quinolyl, isoquinolyl, benzofuryl, benzothienyl, pyrimidyl, pyrazinyl, quinazolyl, phthalazinyl, naphthyridinyl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, COR$^7$, —CN, =O, forming a carbonyl group, or R$^2$ and R$^3$ may be taken together to form a ring comprising:

—CHR$^6$—CHR$^6$—CHR$^6$—, —CHR$^6$—CHR$^6$—CHR$^6$—CHR$^6$—, —CHR$^6$—CR$^6$=CR$^6$—, —CHR$^6$—CHR$^6$—CHR$^6$—CR$^6$=, —CHR$^6$—CHR$^6$—CR$^6$=CR$^6$—, —CHR$^6$—CR$^6$=CHR$^6$—CHR$^6$—, —CR$^6$=CHR$^6$—CHR$^6$—CR$^6$=, —CR$^6$=CHR$^6$—CR$^6$=CR$^6$—, and —CHR$^6$—CR$^6$=CHR$^6$—CR$^6$=;

R$^4$ may be aryl optionally substituted with 1-3 of the following:

$C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN, or R$^4$ may be a heterocyclic ring system selected from the group including:

furyl, thienyl, pyrrolyl, pyridyl, indolyl, quinolyl, isoquinolyl, benzofuryl, benzothienyl, pyrimidyl, pyrazinyl, quinazolyl, phthalazinyl, naphthyridinyl;

R$^5$ is independently selected at each occeurrence from the group including:

hydrogen, $C_1$-$C_{14}$ alkyl, $C_3$-$C_8$ cycloalkyl, $C_1$-$C_6$ alkanoyl, and aryl;

R$^6$ is independently selected at each occurrence from the group including:

hydrogen, phenyl, benzyl, phenethyl, phenoxy, benzyloxy, halogen, hydroxy, nitro, cyano, $C_1$-$C_5$ alkyl, $C_3$-$C_{10}$ cycloalkyl, $C_3$-$C_6$ cycloalkylmethyl, $C_7$-$C_{10}$ arylalkyl, $C_1$-$C_4$ alkoxy, —NR$^7$R$^8$, $C_2$-$C_6$ alkoxyalkyl, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —SO$_2$R$^7$, —S(=O)R$^7$, —SO$_2$NR$^7$R$^8$, —SO$_3$H, —CF$_3$, —OR$^7$, —CHO, —CH$_2$OR$^7$, —CO$_2$R$^7$, —C(=O)R$^7$, —NHSO$_2$R$^8$, —OCH$_2$CO$_2$H, or a 5- or 6-membered heterocyclic ring containing from 1 to 4 heteroatoms selected from oxygen, nitrogen or sulfur;

R$^7$ is H, phenyl, benzyl or $C_1$-$C_6$ alkyl;
R$^8$ is H or $C_1$-$C_4$ alkyl;
or R$^7$R$^8$ can join to form —(CH$_2$)$_4$—, —(CH$_2$)$_5$—, —(CH$_2$CH$_2$N(R$^9$)CH$_2$CH$_2$)—, or —(CH$_2$CH$_2$OCH$_2$CH$_2$)—;

R$^9$ is H or CH$_3$; and
the A ring may contain one double bond;
with the following provisos:

(1) when R$^2$ and R$^3$ are on the same atom, neither R$^2$ nor R$^3$ can be OH;

(2) when n=1 and R$^2$ is 5-hydroxy and R$^3$ is 6-alkoxy and the A ring contains no double bond, then R$^1$ cannot be —CH$_2$CH$_2$Ph or —CH$_2$CH$_2$(3-indolyl) or —CH$_2$CH$_2$(naphthyl);

(3) when n=1 and R$^2$ is 5-hydroxy or 5-acyloxy and R$^3$ is alkoxy and the A ring contains no double bond, then R$^1$ cannot be —(CH$_2$)$_p$aryl or —(CH$_2$)$_p$heteroaryl wherein p=1-3 and the aryl or heteroaryl groups are substituted with 1-3 R$^7$;

(4) when n=2 and R$^2$ is 3-alkyl optionally substituted with cycloalkyl or aryl groups, 3-alkenyl, 3-cycloalkyl, 3-cycloalkenyl, 3-fluorenyl, 3-CHCNPh, 3-CHNO$_2$Ph, or 3-CH(CO$_2$R$^5$)$_2$, and R$^3$ is 5-(=O) and the A ring has no double bond, then R$^1$ cannot be —(CH$_2$)$_r$Aryl wherein r=1-4.

PREFERRED EMBODIMENTS

Preferred compounds in the present invention are those compounds of formula (I) wherein:

n=1 or 2;
R$^1$ is $C_1$-$C_6$ alkyl substituted with 1 or more R$^4$ or $C_4$-$C_{10}$ cycloalkylalkyl;
R$^2$ is H, OH or =O;
R$^3$ is H, $C_1$-$C_8$ alkyl substituted with 0-3 R$^4$ or phenyl optionally substituted with 1-3 F, Cl, Br, NO$_2$, CN, $C_1$-$C_8$ alkyl, and aryl, provided that phenyl is not in the 2- or 3-position;

R$^4$ may be aryl optionally substituted with 1-3 of the following:

$C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN, or R$^4$ may be a heterocyclic ring system selected from the group including:

furyl, thienyl, pyrrolyl, pyridyl, indolyl, quinolyl, isoquinolyl, benzofuryl, benzothienyl, pyrimidyl, pyrazinyl, quinazolyl, phthalazinyl, naphthyridinyl;

R$^5$ is independently selected at each occeurrence from the group including:

hydrogen, $C_1$-$C_{14}$ alkyl, $C_3$-$C_8$ cycloalkyl, $C_1$-$C_6$ alkanoyl, and aryl;

R$^7$ is H, phenyl, benzyl or $C_1$-$C_6$ alkyl; and the A ring may contain one double bond; with the following provisos:

(1) when n=1 and R$^2$ is not present and R$^3$ is not present and the A ring contains a double bond between carbons 5 and 6, then R$^1$ cannot be —CH$_2$Ph;

(2) when n=1 and R$^2$ is 5-OH and R$^3$ is not present and the A ring contains no double bond, then R$^1$ cannot be —CH$_2$Ph;

(3) when n=1 and R$^2$ is 5-keto and R$^3$ is not present and the A ring contains no double bond, then R$^1$ cannot be —CH$_2$Ph;

(4) when n=1 and R$^2$ is not present and R$^3$ is not present and the A ring has a double bond between the 5 and 6 carbons, then R$^1$ cannot be —CH$_2$CH$_2$(3-indolyl);

(5) when n=1 and R$^2$ is not present and R$^3$ is not present and the A ring contains no double bond, then R$^1$ cannot be —CH$_2$CHCH$_3$CH$_2$(4-t-butylphenyl);

(6) when n=2 and R$^2$ is 3-OH or and R$^3$ is not present and the A ring contains no double bond, then R$^1$ cannot be —CH$_2$Ph;

(7) when n=2 and R$^2$ is not present and R$^3$ is not present and the A ring contains a double bond between the 2 and 3 carbons, then R$^1$ cannot be CH$_2$Ph.

More preferred in the present invention are compounds of formula (I) wherein:

n=1 or 2;
R$^1$ is H or $C_1$-$C_6$ alkyl substituted with 1 R$^4$ wherein 1-3 carbon atoms are between N and R$^4$;
R$^2$ is H, OH or =O;
R$^3$ is H or $C_1$-$C_8$ alkyl;
R$^4$ may be aryl optionally substituted with 1-3 of the following:

$C_1$–$C_8$ alkyl, $C_2$–$C_8$ alkenyl, $C_3$–$C_8$ cycloalkyl, $C_1$–$C_6$ perfluoroalkyl, aryl, —F, —Cl, —Br, —I, —$NO_2$, —$OR^5$, —OC(=O)$R^7$, —$N(R^7)_2$, —$SR^5$, —S(O)$R^5$, —$SO_2R^5$, —$CO_2R^7$, —CN, or $R^4$ may be a heterocyclic ring system selected from the group including:

furyl, thienyl, pyrrolyl, pyridyl, indolyl, quinolyl, isoquinolyl, benzofuryl, benzothienyl, pyrimidyl, pyrazinyl, quinazolyl, phthalazinyl, naphthyridinyl;

$R^5$ is independently selected at each occeurrence from the group including:

hydrogen, $C_1$–$C_{14}$ alkyl, $C_3$–$C_8$ cycloalkyl, $C_1$–$C_6$ alkanoyl, and aryl;

$R^7$ is H, phenyl, benzyl or $C_1$–$C_6$ alkyl; and the A ring may contain one double bond; with the following provisos:

(1) when $n=1$ and $R^2$ is not present and $R^3$ is not present and the A ring contains a double bond between carbons 5 and 6, then $R^1$ cannot be —$CH_2Ph$;

(2) when $n=1$ and $R^2$ is 5-OH and $R^3$ is not present and the A ring contains no double bond, then $R^1$ cannot be —$CH_2Ph$;

(3) when $n=1$ and $R^2$ is 5-keto and $R^3$ is not present and the A ring contains no double bond, then $R^1$ cannot be —$CH_2Ph$;

(4) when $n=1$ and $R^2$ is not present and $R^3$ is not present and the A ring has a double bond between the 5 and 6 carbons, then $R^1$ cannot be —$CH_2CH_2$(3-indolyl);

(5) when $n=1$ and $R^2$ is not present and $R^3$ is not present and the A ring contains no double bond, then $R^1$ cannot be —$CH_2CHCH_3CH_2$(4-t-butylphenyl);

(6) when $n=2$ and $R^2$ is 3-OH or and $R^3$ is not present and the A ring contains no double bond, then $R^1$ cannot be —$CH_2Ph$;

(7) when $n=2$ and $R^2$ is not present and $R^3$ is not present and the A ring contains a double bond between the 2 and 3 carbons, then $R^1$ cannot be $CH_2Ph$.

Most preferred in the present invention are compounds of formula (I) wherein:

$n=1$;

$R^1$ is $C_1$–$C_6$ alkyl substituted with 1 $R^4$ wherein 1-3 carbon atoms separate N from $R^4$;

$R^2$ is H;

$R^3$ is H or is $C_1$–$C_8$ alkyl;

$R^4$ may be aryl optionally substituted with 1-3 of the following:

$C_1$–$C_8$ alkyl, $C_2$–$C_8$ alkenyl, $C_3$–$C_8$ cycloalkyl, $C_1$–$C_6$ perfluoroalkyl, aryl, —F, —Cl, —Br, —I, —$NO_2$, —$OR^5$, —OC(=O)$R^7$, —$N(R^7)_2$, —$SR^5$, —S(O)$R^5$, —$SO_2R^5$, —$CO_2R^7$, —CN, or $R^4$ may be a heterocyclic ring system selected from the group including:

furyl, thienyl, pyrrolyl, pyridyl, indolyl, quinolyl, isoquinolyl, benzofuryl, benzothienyl, pyrimidyl, pyrazinyl, quinazolyl, phthalazinyl, naphthyridinyl;

$R^5$ is independently selected at each occeurrence from the group including:

hydrogen $C_1$–$C_{14}$ alkyl, $C_3$–$C_8$ cycloalkyl, $C_1$–$C_6$ alkanoyl, and aryl;

$R^7$ is H, phenyl, benzyl or $C_1$–$C_6$ alkyl; and the A ring may contain one double bond; with the following provisos:

(1) when $n=1$ and $R^2$ is not present and $R^3$ is not present and the A ring contains a double bond between carbons 5 and 6, then $R^1$ cannot be —$CH_2Ph$;

(2) when $n=1$ and $R^2$ is 5-OH and $R^3$ is not present and the A ring contains no double bond, then $R^1$ cannot be —$CH_2Ph$; (3) when $n=1$ and $R^2$ is 5-keto and $R^3$ is not present and the A ring contains no double bond, then $R^1$ cannot be —$CH_2Ph$;

(4) when $n=1$ and $R^2$ is not present and $R^3$ is not present and the A ring has a double bond between the 5 and 6 carbons, then $R^1$ cannot be —$CH_2CH_2$(3-indolyl);

(5) when $n=1$ and $R^2$ is not present and $R^3$ is not present and the A ring contains no double bond, then $R^1$ cannot be —$CH_2CHCH_3CH_2$(4-t-butylphenyl);

(6) when $n=2$ and $R^2$ is 3-OH or and $R^3$ is not present and the A ring contains no double bond, then $R^1$ cannot be —$CH_2Ph$;

(7) when $n=2$ and $R^2$ is not present and $R^3$ is not present and the A ring contains a double bond between the 2 and 3 carbons, then $R^1$ cannot be $CH_2Ph$.

Specifically preferred compounds of the present invention, named according to Chemical Abstracts approved nomenclature rules, are:

a) cis-2-(4-trifluoromethylbenzyl)-3a,4,7,7a-tetrahydroisoindoline;

b) cis-4-chlorophenethylhexahydroisoindole;

c) trans-2-phenethylhexahydroisoindoline;

d) cis-2-phenethylhexahydroisoindoline.

In the present invention it has been discovered that the compounds above are useful as agents to treat physiological or drug induced psychosis and as antidyskenetic agents. Also provided are pharmaceutical compositions containing compounds of Formula (I) as described above.

The present invention also provides methods for the treatment of drug induced psychosis or dyskinesia by administering to a host suffering from such drug induced psychosis or dyskinesia a pharmaceutically effective amount of a compound of Formula (I) as described above.

The compounds herein described may have asymmetric centers. All chiral, enantiomeric, diastereomeric, and racemic forms are included in the present invention. Thus, the compounds of Formula (I) may be provided in the form of an individual stereoisomer, a non-racemic stereoisomer mixture, or a racemic mixture.

Many geometric isomers of olefins, C=N double bonds, and the like can also be present in the compounds described herein, and all such stable isomers are contemplated in the present invention.

When any variable occurs more than one time in any constituent or in Formula (I), or any other formula herein, its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms. The number of carbon atoms in a group is specified herein, for example, as $C_1$–$C_5$ to indicate 1-5 carbon atoms. As used herein "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Cycloalkyl-alkyl" is intended to include cycloalkyl attached to alkyl. "Halo" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; "carbocyclic" is intended to mean any stable 5- to 7- membered monocyclic or bicyclic or 7- to 14-membered bicyclic or tricyclic carbon ring, any of which may be saturated, partially unsaturated, or aromatic, for example, indanyl or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, pyrazinyl, quinazoyl, phthalazinyl, naphthyridinyl or octahydroisoquinolinyl.

The term "substituted", as used herein, means that one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive to a useful degree of purity from a reaction mixture, and formulation into an efficacious therapeutic agent.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton Pa., 1985 p. 1418, the disclosure of which is hereby incorporated by reference.

DETAILED DESCRIPTION OF THE INVENTION

The compounds disclosed in this section are numbered according to Chemical Abstracts rules.

Methods of Preparation (1) Hydroisoindolines

Diels-Alder reaction of butadiene or substituted butadienes with maleic anhydride or substituted maleic anhydrides is known to give adducts of type 1. Reaction of these adducts with amines $R^1NH_2$ and

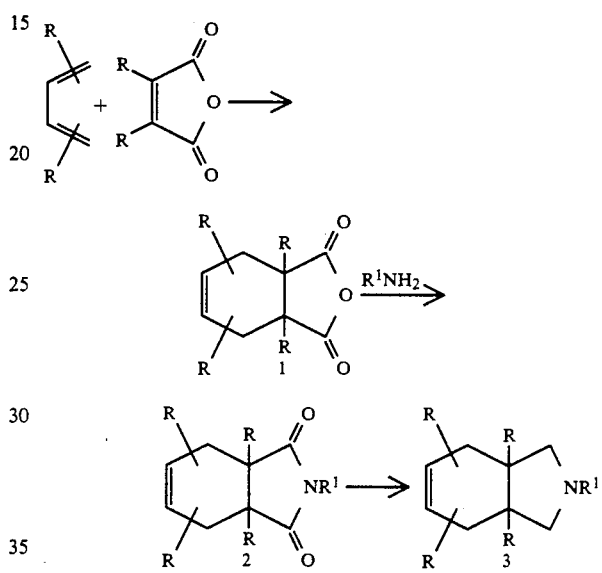

dehydration of the intermediate maleamic acids gives imides of type 2 which on reduction with complexed metal hydrides such as lithium aluminum hydride or sodium bis(methoxyethoxy) aluminum hydride gives the amines 3 of this invention. The double bond can be removed by catalytic hydrogenation in either intermediates 1 or 2 or in the final product 3. The double bond may also be moved to 4.5; 3a,4; or 3a,7a-positions by the action of a catalyst, such as a rhodium salt.

Alternatively, the Diels-Alder reaction may be carried out with maleimides (4) which gives imides 2 directly. When $R^1$ contains

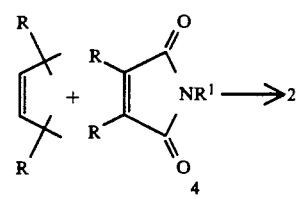

functionalities that are reduced by complexed metal hydrides, the desired products may be obtained by alkylating amines 3 ($R^1$=H) with $R^1 X$ (where X is, for instance, Cl, Br, I, methanesulfonyl, or p-toluenesulfonyl) in the presence of an organic or inorganic base.

When the butadiene component in the Diels-Alder reaction is substituted in the 2-position with a protected hydroxyl group (such as, acetoxy or trimethylsilyloxy groups), compounds of type 5 are obtained which on removal of the protecting by known methods give ketones 6.

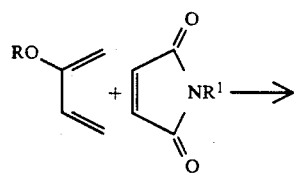

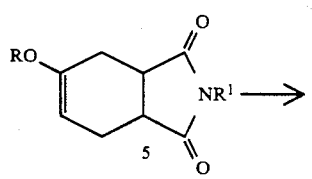

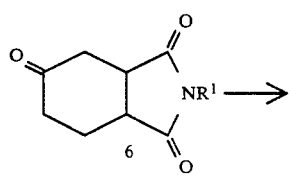

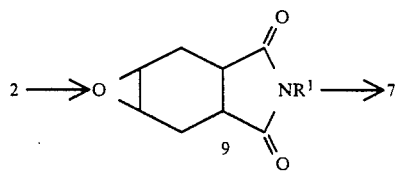

Reduction as described above gives amino alcohols of type 7 which may be oxidized by well-known methods, such as the Swern oxidation, or with pyridine-SO$_3$, to the ketones 8. The latter may alternatively be obtained by converting imides 2 into the corresponding epoxides 9

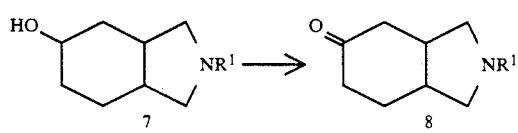

which on reduction, as described above, give the aminoalcohols 7. The latter may be acylated by standard methods.

A similar series of reactions may be carried out with butadienes carrying a protected hydroxyl group in the 1-position:

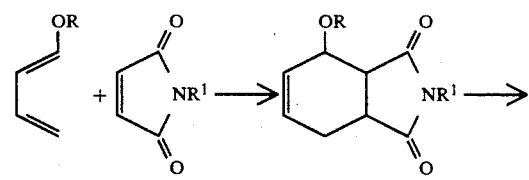

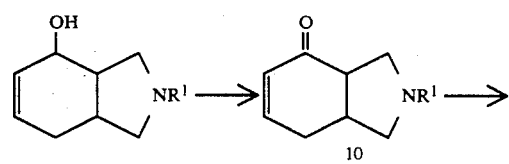

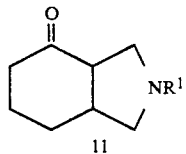

Ketones 8 may be converted into aminoalcohols 12 by reaction with organometallic reagents, such as R$^2$Li or R$^2$MgX (where X is Cl, Br, or I).

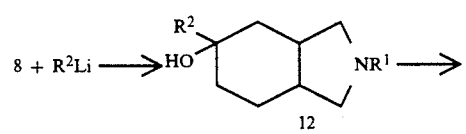

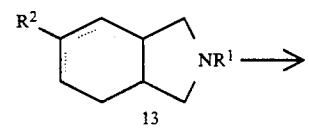

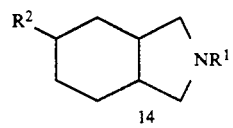

Compounds 12 may be dehydrated by known methods to give the olefinic amines 13 which on catalytic hydrogenation give the saturated amines 14. The same sequence of reactions may be carried out with ketones 11.

Substituents R$^2$ may be introduced into the 3a position by conversion of imides 2 or their saturated analogs into the anion with a strong base such as lithium diisopropylamide followed by treatment with R$^2$X where X=Cl, Br, I, CH$_3$SO$_3$, p—CH$_3$C$_6$H$_4$SO$_3$ or other suitable leaving groups.

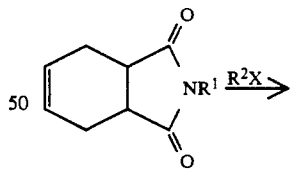

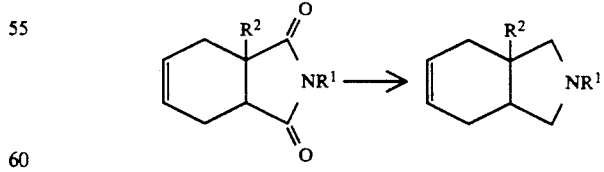

An alternative approach to the hydroisoindoles of the present invention uses the intramolecular Diels-Alder reaction. For instance, diene amides 15, which may be prepared by standard amide-forming reactions from the known acids and amines, cyclize on heating to give lactams 16 which on

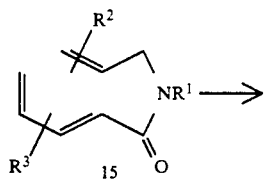

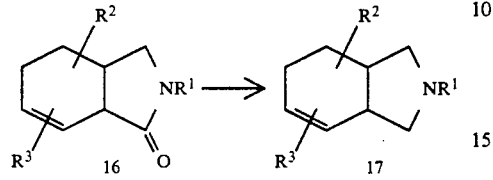

reduction give the amines 17 of this invention. This type of reaction is reviewed in *Organic Reactions*, Vol. 32, Chapter 1. Alternatively, amides of type 18 may be converted via lactams 19 into amines 17. Finally, amines

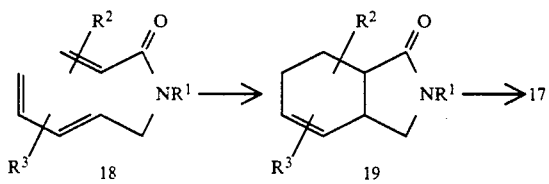

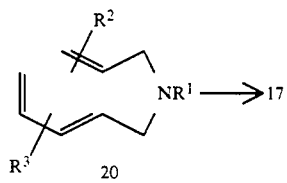

20 may be cyclized to give amines 17 directly. In the latter reaction it may be of advantage to use a protecting group $R^1$ such $CF_3CO$ to facilitate the cyclization. The protecting group is then removed by standard methods to give amines 17 ($R^1$ =H) which are subsequently alkylated with $R^1X$, as described earlier.

(2) Hydroisoquinolines

A large number of hydroisoquinolines having hydrogen on the nitrogen atom may be prepared via known methods (Comprehensive Heterocyclic Chemistry, Pergamon Press, 1982; Vol. 2; Chemistry of Heterocyclic Compounds, Wiley, Vol 38). These may be converted into the compounds of this invention by known methods of introducing substituents $R^1$ on nitrogen, such as, reaction with a reagents $R^1X$ (X=Cl, Br, I, $OSO_2Ar$, $OSO_2Me$, etc.) in the presence of a base

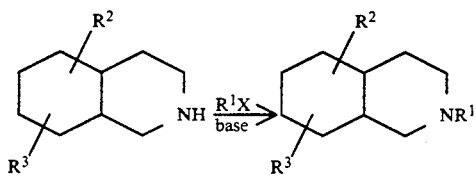

Alternatively, isoquinolines 21 which are known or are available from known

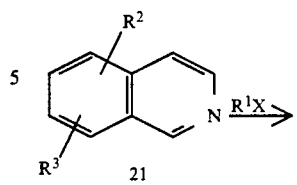

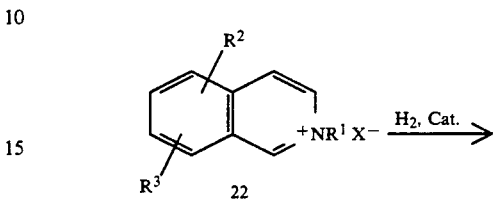

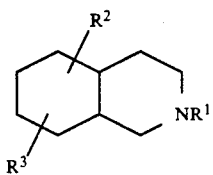

methods, may be quaternized by reaction with $R^1X$ and the quaternary isoquinolinium salts may be reduced by well-known methods with hydrogen in the presence of a catalyst. Tetrahydroisoquinolines 23 are well known and may be prepared by many different methods (cf. the two references given above). These may be treated with $R^1X$ as described above and the compounds so obtained may be reduced with hydrogen and a catalyst to give compounds of this invention.

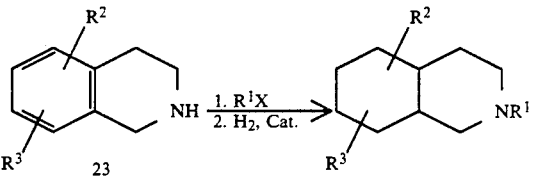

Another approach to the hydroisoquinolines of this invention involves the intramolecular Diels-Alder reaction as described in section 1 above. This approach is illustrated below:

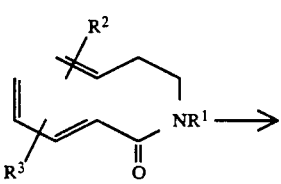

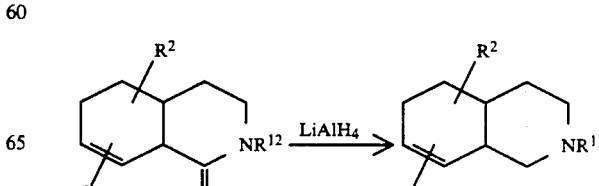

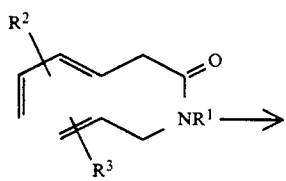

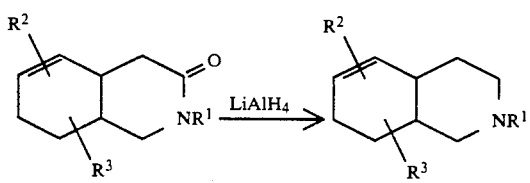

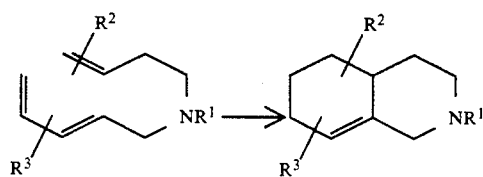

Certain ketones of types 24 and 25 may be obtained by a Robinson annellation of piperidones (cf. for instance, L. Augustine, *J. Org. Chem.*, 33,

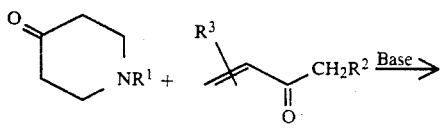

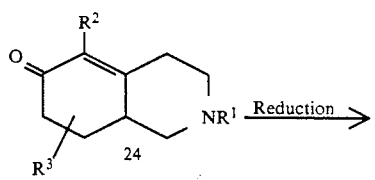

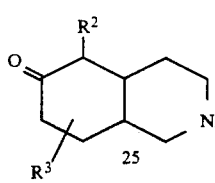

1853 (1958)). Ketones 24 and 25 may be modified further. Thus, reduction with complexed metal hydrides, such as sodium borohydride or lithium aluminum hydride gives alcohols, e.g. 26 which may be converted

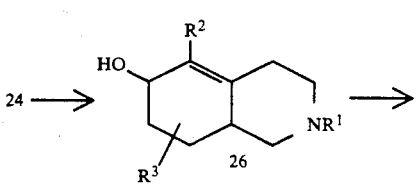

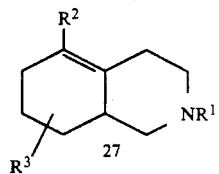

into compounds 27 by known methods for the removal of hydroxyl groups, for instance, by conversion into the toluenesulfonate followed by reduction. 1,2-Addition of organometallic reagents to ketones 24 or 25 gives substituted alcohols, e.g. 28 in which the hydroxyl groups may also be removed as indicated above to give compounds 29. 1,4,-addition of

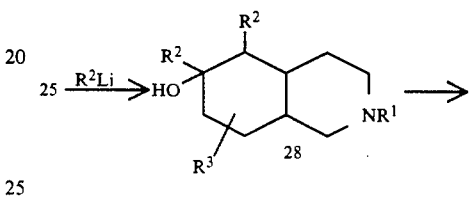

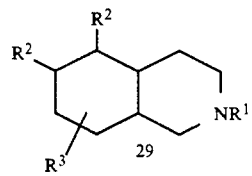

organocuprates to ketones 24 gives 4a-substituted derivatives 30 (Bartmann et al., Synthetic Communications, 18, 711 (1988)). These may

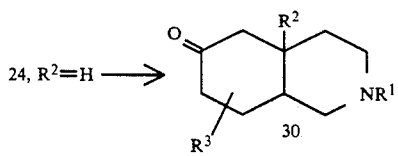

be further modified as described above for ketones 24 and 25.

EXAMPLES

Analytical data were recorded for the compounds described below using the following general procedures. Proton NMR spectra were recorded on a Varian FT-NMR spectrometer (200 MHz or 300 MHz); chemical shifts were recorded in ppm (∂) from an internal tetramethylsilane standard in deuterochloroform or deuterodimethylsulfoxide and coupling constants (J) are reported in Hz. Mass spectra (MS) or high resolution mass spectra (HRMS) were recorded on Finnegan MAT 8230 spectrometer or Hewlett Packard 5988A model spectrometer. Melting points are uncorrected. Boiling points are uncorrected.

Reagents were purchased from commercial sources and, where necessary, purified prior to use according to the general procedures outlined by D. D. Perrin and W. L. F. Armarego, Purification of Laboratory Chemicals, 3rd ed., (New York: Pergamon Press, 1988). Chromatography was performed on silica gel using the solvent systems indicated below. For mixed solvent systems, the volume ratios are given. Parts and percentages are by weight unless otherwise specified. Common abbreviations include: THF (tetrahydrofuran), TBDMS (t-butyl-dimethylsilyl), DMF (dimethylformamide), Hz (hertz) TLC (thin layer chromatography).

The exemplified compounds are named according to the Chemical Abstract reulres of nomenclature.

EXAMPLE 1 cis-2-(4-Fluorophenethyl)-3a,4,7,7a-tetrahydroisoindoline

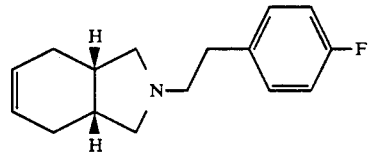

A solution of 9.3 g of 1,2,3,6-tetrahydrophthalic anhydride in 30 mL of dry THF was treated with 8.08 g of 4-fluorophenethylamine, heated under reflux for 30 mins. and concentrated under vacuum. The residual solid was heated with stirring in a 160°-oil bath for 1 hour and the product was recrystallized from 1-chlorobutane to give 10.32 g. of N-(4-fluorophenethyl)-1,2,3,4-tetrahydrophthlalimide.

To 2.0 g of the above intermediate in 20 mL of dry THF was added with cooling 16 mL of 1 M lithium aluminum hydride in THF and the mixture was heated under reflux for 2 hours. Water (0.64 mL), 15% aqueous sodium hydroxide solution (0.64 mL), and water (1.8 mL) were added sequentially, with cooling. The solids were removed by filtration and washed several times with methylene chloride. The combined filtrates were concentrated and the residue was short-path distilled (150° bath temperature, 0.001 mm) to give 1.63 g of 2-(4-fluorophenethyl-3a,3,7,7a-tetrahydroisoindoline. $^1$H-NMR (in CDCl$_3$) $\delta$7.2 (m, 2H); 7.0 (m, 2H); 5.8 (m, 2H); 3.0 (m, 2H); 2.6–2.8 (m, 4H); 2.4 (m, 2H); 2.1–2.3 (m, 4H) and 1.9 (d, 2H). The fumarate had m.p. 125°–126° after crystallization from 2-propanol.

Anal. Calcd. for $C_{20}H_{24}FNO_4$: C, 66.46; H, 6.69; N, 3.88; Found: C, 66.63; H, 6.63; N, 3.67.

EXAMPLE 2 cis-2-(4-Fluorophenethyl)hexahydroisoindoline

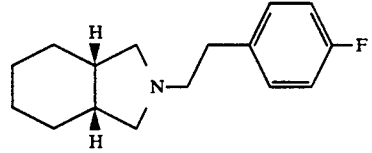

A mixture of 0.44 g of cis-2-(4-fluorophenethyl)-3a,4,7,7a-tetrahydroisoindoline (Ex. 1), 7 mL of ethanol and 0.08 g of prereduced PtO$_2$ was stirred under hydrogen for 1 hr. 20 mins. The catalyst was removed by filtration, the filtrate was concentrated and the residue was short-path distilled (140° bath, 0.002 mm) to give 0.41 g. of cis-2-(4-fluorophenethyl)hexahydroisoindoline. $^1$H NMR (in CDCl$_3$) $\delta$7.2 (d/d, 2H); 7.0 (t, 2H); 2.8 (d/d, 2H); 2.7 (s, 4H), 2.5 (d/d, 2H); 2.2 (m, 2H) and 1.2–1.6 (m, 8H). The fumarate had m.p.130°–131° after crystallization from 2-propanol.

Anal. Calcd. for $C_{20}H_{26}FNO_4$: C, 66.10; H, 7.21; N, 3.85; Found: C, 66.14; H, 7.14; N, 3.80.

EXAMPLE 3 trans-2-Phenethylhexahydroisoindoline

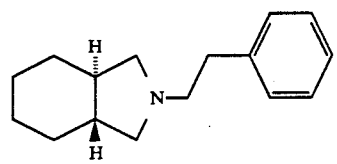

Phenethylamine (11.9 g) was added slowly to a mixture of 15.16 g of trans-hexahydrophthalic anhydride and 50 mL of THF. After the exothermic reaction had subsided, the solvent was removed under vacuum to give 25.2 g of a solid. A mixture of 11.15 g of this solid and 50 mL of acetyl chloride was heated under reflux for 20 mins., the excess reagent was removed under vacuum and the residue was dissolved in 200 mL of methylene chloride. The solution was treated with 10% aqueous sodium carbonate to a basic PH, the layers were separated and the aqueous layer was extracted several times with methylene choride to give 9.21 g of crude product. Crystallization from 15 mL of 2-propanol gave 6.73 g of trans-2-phenethylhexahydrophthalimide.

To a solution of 1.27 g of the imide in 10 mL of dry THF were added 15 mL of 1 M lithium aluminum hydride in THF and the mixture was heated under reflux for 6 hours. Isolation by the procedure given in Example 1 and short-path distillation (140° bath, 0.001 mm) gave 1.12 g. of trans-2-phenethylhexahydroisoindoline. $^1$H-NMR (in CDCl$_3$) $\delta$7.2–7.3 (m, 5H); 2.9 (d/d, 2H); 2.8(s, 4H); 2.4 (t, 2H); 1.7–1.9 (m, 4H), 1.5 (m, 2H), 1.2 (m, 2H) and 1.1 (m, 2H). The fumarate had m.p. 170°–171° (dec.) after crystallization from ethanol.

Anal. Calcd. for $C_{20}H_{27}NO_4$: C, 69.54; H, 7.88; N, 4.05; Found: C, 69.44; H, 7.74; N, 3.97.

EXAMPLE 4 cis-2-(4-Pyridylethyl)-3a,4,7,7a-tetrahydroisoindoline

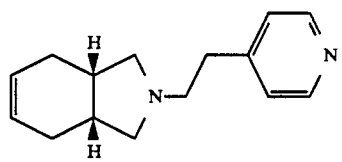

A mixture of 0.64 g of cis-3a,4,7,7a-tetrahydroisoindoline, 0.6 mL of 4-vinylpyridine, 0.4 mL of acetic acid and 10 mL of methanol was heated under reflux for 16 hours. Removal of the solvent and short-path distillation of the residue (160° bath temperature, 0.002 mm) gave 0.74 g. of cis-2-(4-pyridylethyl)-3a,4,7,7a-tetrahydropyridine. $^1$H NMR (in CDCl$_3$) $\delta$8.5 (d, 2H); 7.1 (d, 2H); 5.8 (m, 2H); 3.0 (m, 2H); 2.7-2.8(m, 4H); 2.4 (m, 2H); 2.2–2.3 (m, 4H) and 1.9 (d, 2H). The dihydrochloride hemi-hydrate had an indefinite melting point after crystallization from 2-propanol.

Anal. Calcd. for $C_{15}H_{22}Cl_2N_2 \cdot \frac{1}{2}H_2O$: C, 58.07; H, 7.47; N, 9.03; Found: C, 58.27; H, 7.47; N, 9.15.

EXAMPLE 5 cis-5-Hydroxy-2-phenethylhexahydroisoindoline

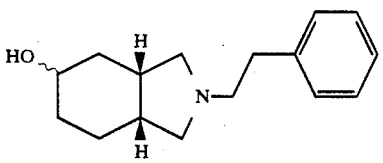

A mixture of 10 g of cis-2-phenethyl-3a,4,7,7a-tetrahydroisoindoline (prepared by the method of Example 1), 80 mL of chloroform and 12 g. of m-chloroperoxybenzoic acid was stirred at room temperature for 30 mins. Methylene chloride (200 mL) and 15% aqueous sodium hydroxide (100 mL) were added and the dried organic phase was concentrated to give 10.2 g of crude cis-5,6-epoxy-2-phenethylhexahydroisoindoline as a mixture of two isomers.

To 8.5 g of the above product in 80 mL of dry THF was added at 0°, 80 mL of 1 M lithium aluminum hydride in THF. The mixture was stirred in an ice bath for 1 hour, then refluxed for 6 hours. Isolation as described in Example 1 gave 7.00 g of crude product which on short-path distillation (180° bath temperature, 0.001 mm) gave 6.10 g. of cis-5-hydroxy-2-phenethylhexahydroisoindoline (mixture of two isomers) as an oil. The fumarate had m.p. 118°–126° after crytallization from 2-propanol.

Anal Calcd. for $C_{20}H_{27}NO_5$; C, 66.46; H, 7.53; N, 3.88; Found: C, 66.37; H, 7.51; N, 3.81.

EXAMPLE 6 cis-2-Phenethylhexahydroisoindolin-5-one

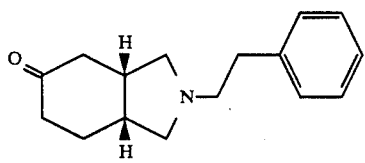

To a solution of 0.68 g of cis-5-hydroxy-2-phenethylhexahydroisoindoline (Example 5) in 6 mL of dry dimethylsulfoxide and 5 mL of triethylamine was added a solution of 1.82 g $SO_3$.pyridine in 7 mL of dry DMSO. After stirring at room temperature for 4 hours, 20 mL of 15% sodium hydroxide solution was added with cooling and the solution was extracted with toluene to give 0.63 g of product. Short-path distillation (160° bath temperature, 0.001 mm) gave 0.51 g of cis-2-phenethylhexahydroisoindolin-5-one as an oil. The fumarate had m.p. 130°–134° (dec.) after crystallization from 2-propanol.

Anal. Calcd. for $C_{20}H_{25}NO_5$: C, 66.83; H, 7.01; N, 3.90; Found: C, 66.45; H, 7.13; N, 3.79

EXAMPLE 7 cis-2-Phenethyl-3a,4,5,7a-tetrahydroisoindoline

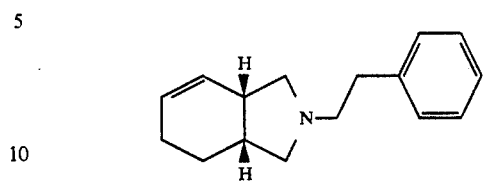

A mixture of 5.0 g of cis-N-phenethyl-1,2,3,6-tetrahydrophthalimide (prepared by the method of Example 1), 0.5 g of chlorotris(triphenylphosphine)rhodium and 50 mL of p-xylene was heated under reflux for 48 hours. Removal of the solvent and short-path distillation of the residue (150° bath temperature, 0.001 mm) gave 4.72 g of cis-N-phenethyl-1,2,3,4-tetrahydrophthalimide containing 12% of unrearranged starting material.

To a solution of 2.04 g of the above product in 15 mL of dry THF was added, with cooling, 20 mL of 1 M lithium aluminum hydride in THF. The mixture was heated under reflux for 6 hours. Isolation as described in Example 1 and short-path distillation of the residue (150° bath temperature, 0.001 mm) gave 1.39 g of cis-2-phenethyl-3a,4,5,7a-tetrahydroisindoline containing ca. 10% of cis-2-phenethyl-3a,4,7,7a-tetra-hydroisoindoline. $^1$H NMR (in $CDCl_3$) : δ7.1–7.3 (m, 5H); 5.8 (m, 1H); 5.7 (d, split further, 1H); 3.0–3.1 (m, 2H); 2.8 (m, 2H); 2.7 (m, 2H); 2.4 (m, 1H); 2.1–2.3 (m, 2H); 2.0 (m, 2H); 1.8(m, 1H); 1.7 (m, 1H) and 1.4 (m, 1H). The fumarate had m.p. 145°–148° (dec.) after two crystallizations from ethanol.

Anal. Calcd. for $C_{20}H_{25}NO_4$; C, 69.94; H, 7.34; N, 4.08; Found: C, 69.62; H, 7.25; N, 3.97.

EXAMPLE 8

5-Methyl-2-phenethyl-3a,4,5,7a-tetrahydroisoindoline

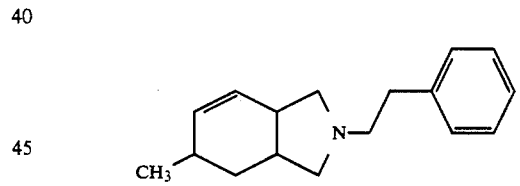

Sorboyl chloride (3.53 g) was added to a mixture of 4.0 g of N-allylphenethylamine, 25 mL of methylene chloride and 25 mL of 15% aqueous sodium hydroxide, keeping the temperatue below 15°. The mixture was stirred in an ice bath for 1 hour, then at room temperature overnight. The aqueous layer was extracted several times with toluene and the combined organic phases were washed successively with 5% hydrochloric acid, water, and 10% sodium carbonate solution. Removal of the solvents gave 6.37 g of N-allyl-N-phenethylsorbamide. This product was heated under reflux in 50 mL of p-xylene for 10 hours. Removal of the solvent gave 6-methyl-3a,4,5,7a-tetrahydroisoindolin-1-one as a mixture of isomers still containing about 10% of the uncyclized starting material.

To a solution of this material in 30 ml of dry THF was added 50 mL of 1 M lithium aluminum hydride in THF and the mixture was heated under reflux for 22 hours. Isolation as described in Example 1 followed by purification by way of the hydrochloride gave 4.50 g of crude product. Short-path distillation (125° bath temperature, 0.001 mm) gave 2.25 g of 5-methyl-2-phenethyl-3a,4,5-,7a-tetrahydroisoindoline as a mixture of two isomers. 'H-NMR (in CDCl$_3$) δ7.1–7.3 (m,5H); 5.6–5.7 (m, 2H) and 1.0 (2d,3H), among others. The fumarate had m.p. 141°–146° after crystallization from 2-propanol.

Anal. Calcd. for C$_{21}$H$_{27}$NO$_4$: C, 70.56; H, 7.61; N, 3.92; Found: C, 70.33; H, 7.53; N, 3.88

EXAMPLE 9 cis-2-(4-Bromophenethyl)-3a,4,7,7a-tetrahydroisoindoline

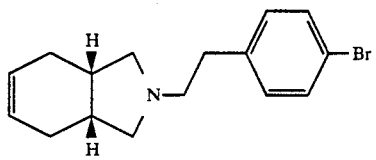

A mixture of 0.6 g of cis-3a,4,7,7a-tetrahydroisoindoline, 1.4 g of 4-bromophenethyl bromide, 1.0 g of potassium carbonate and 3 mL of dimethylformamide was stirred and heated in a 90° oil bath for 1 hour. Toluene (20 mL) and water (20 mL) were added and the aqueous layer was extracted with toluene. Addition of 10 mL of 10% hydrochloric acid to the toluene solution resulted in the formation of three layers. The two lower layers were made basic with aqueous sodium hydroxide solution. Extraction with methylene chloride gave 0.89 g of crude product which on short-path distillation gave 0.63 g of cis-2-(4-bromophenethyl)-3a,4,7,7a-tetrahydroisoindoline. 'H NMR (in CDCl$_3$) δ7.4 (d, 2H); 7.0 (d, 2H); 5.8 (m, 2H); 3.0 (m, 2H); 2.6-2.8 (m, 4H); 2.4 (m, 2H); 2.1–2.3 (m, 4H) and 1.9 (d, 2H). The fumarate had m.p. 166°–167° after crystallization from ethanol.

Anal. Calcd. for C$_{20}$H$_{24}$BrNO$_4$: C, 56.88; H, 5.73; N, 3.32; Found: C, 56.91; H, 5.64; N, 3.21

EXAMPLE 10 cis-2-(3,4-Dichlorophenethyl)-3a,4,7,7a-tetrahydroisoindoline

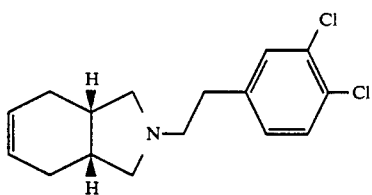

To a solution of 1.13 g of 3,4-dichlorophenylacetic acid in 6 mL of THF was added 0.90 g of 1,1'-carbonyldiimidazole. After 30 minutes a solution of 0.61 g of cis-3a,4,7,7a-tetrahydroisoindoline in 2 mL of THF was added and the mixture was stirred at room temperature overnight. Toluene (50 mL) was added, and the solution was washed successively with 5% hydrochloric acid, water, and 10% aqueous sodium carbonate solution, dried, and concentrated to give 1.50 g of cis-2-(3,4-dichlorophenylacetyl)-3a,4,7,7a-tetrahydroisoindole.

To 0.70 g of this intermediate and 3 mL of toluene was added at 0° 2 mL of 3.4 M sodium bis(2-methoxyethoxy)aluminum hydride in toluene and the mixture was stirred in an ice bath for 1 hour and at room temperature for 4 hours. Aqueous sodium hydroxide solution (15%, 5 mL) and water (10 mL) were added with cooling. From the toluene layer there was obtained 0.66 g of crude product which was partitioned into a neutral and basic fraction. The latter was short-path distilled (140° bath temperature, 0.003 mm) to give 0.48 g of cis-2-(3,4-dichlorophenethyl)-3a,4,7,7a-tetrahydroisoindoline. 'H NMR (in CDCl$_3$) : δ7.3 (AB quartet, 2H);7.0 (d/d, 1H); 5.8 (m, 2H); 3.0 (m, 2H); 2.8 (m, 4H), among others. The hydrochloride had m.p. 201°–202° after recrystallization from ethanol.

Anal. Calcd. for C$_{16}$H$_{20}$Cl$_3$N : C, 57.76; H, 6.06; N, 4.21; Found: C, 57.86; H, 6.04; N, 4.09.

EXAMPLE 11

2-Phenethyldecahydroisoquinoline

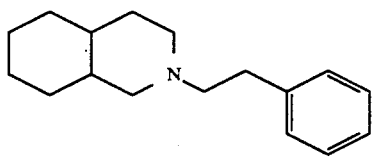

To 5.0 g of decahydroisoquinoline (mixture of cis and trans isomers), 20 mL of methylene chloride and 50 mL of 15% aqueous sodium hydroxide solution was added at 10°–15° a solution of 7 mL of phenylacetyl chloride in 20 mL of methylene chloride. Removal of the solvent from the dried organic layer and crystallizaiton of the residue from hexanes gave 3.12 g of 2-phenylacetyldecahydroisoquinoline.

To a solution of 0.5 g of the above intermediate in 10 mL of dry THF was added, with cooling, 4 mL of 1 M lithium aluminum hydride in THF. The mixture was heated under reflux for 6 hours and the product was isolated as described in Example 1. Short-path distillation (140° bath temperature, 0.001 mm) gave 0.43 g of 2-phenethyldecahydroisoquinoline. The fumarate had m.p. 169°–170° after crystallization from 2-propanol.

Anal. Calcd. for C$_{21}$H$_{29}$NO$_4$: C, 70.17; H, 8.13; N, 3.90; Found: C, 69.92; H, 8.00; N, 3.62

EXAMPLE 12

2-Phenethyl-1,2,3,4,5,6,7,8-octahydroisoquinoline

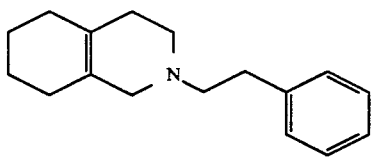

A mixture of 2.05 g of 5,6,7,8-tetrahydroisoquinoline, 4.30 g of 2-bromoethylbenzene, and 5 mL of dimethylformamide was stirred in a 75°–80° oil bath for 4 hours. The solvent was removed under vacuum, the residue was dissolved in 4 mL of acetonitrile and 8 mL of 1-chlorobutane were added. The precipitate was collected after 1 hour to give 3.28 g of 2-phenethyl-5,6,7,8-tetrahydroisoquinolinium bromide.

To a mixture of 2.00 g of the above intermediate and 10 mL of ethanol was added at 0° 0.56 g of sodium borohydride in small portions. Water was added after stirring in an ice bath for 1 hour, and the product was extracted into methylene chloride. Removal of the solvent and short-path distillation of the residue (150°, 0.002 mm) gave 1.28 g of 2-phenethyl-1,2,3,4,5,6,7,8-octahydroisoquinoline. 'H NMR (in CDCl$_3$) δ7.2–7.3

(m, 5H); 2.9 (m, 4H); 2.6 (m, 4H); 2.1 (m, 2H); 1.8 (m, 4H), and 1.6 (m, 4H). The fumarate had m.p. 159°-160° after crystallization from ethanol.

Anal. Calcd. for $C_{21}H_{27}NO_4$: C, 70.56; H, 7.61; N, 3.92; Found: C, 70.50; H, 7.63; N, 3.81.

EXAMPLE 13 cis-2,3a-Dibenzyl-3a,4,7,7a-tetrahydroisoindoline

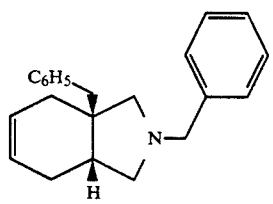

To 0.99 mL (7.1 mmoles) of diisopropylamine was added under nitrogen 15 mL of dry THF and the mixture was cooled to −78°. To the solution was then added 3.0 mL of n-butyl lithium (2.15 M in hexanes). The mixture was allowed to warm to room temperature and then recooled to −78°. A mixture of 1.42 g (5.9 mmoles) of cis-2-benzyl-3a,4,7,7a tetrahydro-1H-isoindole-1.3(2H)-dione in 5 mL of dry THF was added to the above solution by cannula, and the transfer was completed using 2×2.5 mL THF. Benzyl bromide (0.70 mL, 5.9 mmoles) was added to the stirred solution via syringe. The mixture was stirred at −78° for 0.5 h and then allowed to warm to room temperature and stirred for another 3 h. To the reaction mixture was added 15 mL of water, and the excess THF was removed by evaporation. The product was extracted with methylene chloride and the combined organic extracts were dried and evaporated to give 2.82 g of a brown oil. Chromatography of the oil on silica gel using hexane-ethyl acetate (2:1) to elute recovered 1.48 g of cis-2,3a-dibenzyl-3a,4,7,7a-tetrahydro-1H-isoindole-1.3(2H)-dione as a yellow oil. NMR (CDCl$_3$): δ7.00-7.27 (m, 10 H); 5.81-5.92 (m, 2H); 4.49 (s, 2H); 3.23-3.31 (d, 1H); 2.88-2.94 (m, 1H); 2.68-2.76 (d, 1H); 2.58-2.67 (m, 2H); 2.01-2.19 (m, 2H).

To 0.70 g (18.4 mmoles) of lithium aluminum hydride in 10 mL of THF was added at 0° 1.46 g (4.4 mmoles) of the above intermediate in 10 mL of THF by cannula. The transfer was completed using 2×2.5 mL of THF. The mixture was refluxed for 18 h and then cooled to 0°. The mixture was quenched by the slow addition of 0.7 mL water, followed by 0.7 mL of 15% aqueous sodium hydroxide solution and then 2.1 mL water. The reaction mixture was stirred at 0° for 15 min., and then the precipitated salts were removed by filtration through celite. The filtrate was evaporated to dryness, and the residue was dissolved in methylene chloride. The organic phase was washed with water, dried and evaporated to give 1.14 g of cis-2,3a-dibenzyl-3a,4,7,7a-tetrahydroisoindoline as a clear oil. NMR (CDCl$_3$): δ7.03-7.38 (m, 10 H); 5.67-5.80 (m, 2H); 3.47-3.67 (q, 2H); 2.74-2.96 (m, 2H); 2.60-2.73 (q, 2H); 2.46-2.55 (t, 2H); 2.06-2.36 (m, 3H); 1.83-2.06 (m, 3H). The fumaric acid salt had m.p. 142°-144° after crystallization from isopropyl alcohol.

Anal Calcd. for $C_{26}H_{29}NO_4$: C, 74.44; H, 6.97; N, 3.34; Found: C, 74.39; H, 6.97; N, 3.29

EXAMPLE 14 cis-2,3a-Dibenzylhexahydroisoindoline

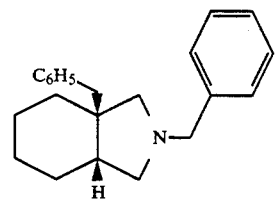

A mixture of 0.46 g (1.3 mmoles) of cis-2,3a-dibenzyl-3a,4,7,7a-tetrahydroisoindoline (Ex. 13), 0.46 g of platinum oxide and 100 mL of methanol were hydrogenated at 50 p.s.i. for 1 h. The catalyst was removed by filtration through celite and the filtrate was evaporated to give 0.41 g of the title compound as a clear oil.

The fumaric acid salt had m.p. 156°-158° after crystallization from isopropyl alcohol. NMR (DMSO-d$_6$): δ7.18-7.38 (m, 10H); 6.57 (s, 2H); 3.75-3.90 (q, 2H); 2.72-3.93 (m, 4H); 2.55-2.63 (d, 1H); 2.43-2.52 (d, 1H); 1.93-2.06 (m, 1H); 1.55-1.60 (m, 1H); 1.21-1.52 (m, 7H).

Anal. Calcd. for $C_{26}H_{31}NO_4$: C, 74.08; H, 7.41; N, 3.32; Found: C, 74.10; H, 7.28; N, 3.21.

Tables I and II contain additional examples prepared by the methods disclosed above.

TABLE I

| Example No. | R$^1$ | R$^2$ | F = fum. H = HCl | m.p. | C calcd | H calcd | N calcd | C found | H found | N found |
|---|---|---|---|---|---|---|---|---|---|---|
| 14a | CH$_2$-(cyclopentyl) | H | F | 203-205d | 66.84 | 9.04 | 4.33 | 67.01 | 9.06 | 4.29 |
| 14b | (CH$_2$)$_2$-(cyclohexyl) | H | F | 164-165° | 68.34 | 9.46 | 3.99 | 68.24 | 9.44 | 3.97 |
| 15 | CH$_2$Ph | H | F | 160-161° | 68.86 | 7.60 | 4.23 | 68.92 | 7.55 | 4.18 |

TABLE I-continued

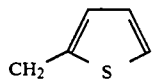

| Example No. | R¹ | R² | F = fum. H = HCl | m.p. | C calcd | H | N | C found | H | N |
|---|---|---|---|---|---|---|---|---|---|---|
| 16 | $CH_2C_6H_4F$-4 | H | F | 123–125° | 65.31 | 6.92 | 4.01 | 64.96 | 6.65 | 3.83 |
| 17 | $CH_2C_6H_4CF_3$-4 | H | F | 167–168° | 60.14 | 6.06 | 3.51 | 60.15 | 5.89 | 3.32 |
| 18 | 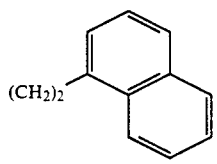 | H | F | 164–165° | 60.51 | 6.87 | 4.15 | 60.38 | 6.79 | 4.04 |
| 19 | $CH_2CH_2Ph$ | H | F | 155–156° | 69.54 | 7.88 | 4.05 | 69.46 | 7.77 | 4.06 |
| 20 | $CH_2CH_2C_6H_4F$-3 | H | H | 230–232d | 67.71 | 8.17 | 4.95 | 67.64 | 8.12 | 4.83 |
| 21 | $CH_2CH_2C_6H_4Cl$-4 | H | F | 162–163°d | 63.23 | 6.90 | 3.69 | 63.23 | 7.21 | 3.52 |
| 22 | $CH_2CH_2C_6H_4OMe$-4 | H | F | 130–131° | 67.18 | 7.79 | 3.73 | 66.81 | 7.66 | 3.70 |
| 23 | $CH_2CH_2C_6H_4OH$-4 | H | H | 180–182° | 68.19 | 8.50 | 4.97 | 68.03 | 8.55 | 4.83 |
| 24 | $CH_2CH_2Ph$ | 3a-Me | F | 157–159°d | 70.17 | 8.13 | 3.90 | 69.99 | 8.11 | 3.82 |
| 25 | $CH_2CH_2C_6H_4F$-4 | 5-OH | free base[a,b] | | | | | | | |
| 26 | $CH_2CHPh_2$ | H | F | 163–165° | 74.08 | 7.41 | 3.32 | 74.18 | 7.31 | 3.24 |
| 27 | 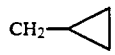 | H | F | 151–152 | 72.89 | 7.39 | 3.54 | 73.01 | 7.30 | 3.46 |
| 28 | $CH_2CH_2CHPh_2$ | H | F | 165–167° | 74.45 | 7.64 | 3.22 | 74.56 | 7.64 | 3.12 |

[a] Mixture of isomers
[b] H NMR spectrum (in $CDCl_3$): δ 7.1(t, split further, 2H); 6.9(t, 2H); 3.8 and 3.6(2m, 1H) and 1.2–3.0(m, 17H)

TABLE II

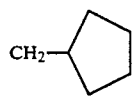

| Example No. | R¹ | R² | F = fum. H = HCl | m.p. | C calcd. | H | N | C found | H | N |
|---|---|---|---|---|---|---|---|---|---|---|
| 29 | 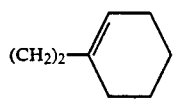 | H | F | 118–120° | 65.51 | 7.90 | 4.77 | 65.51 | 7.90 | 4.77 |
| 30 | $CH_2$-cyclopentyl | H | F | 189–191°d | 67.26 | 8.47 | 4.36 | 67.35 | 8.51 | 4.29 |
| 31 | $(CH_2)_2$-cyclohexenyl | H | F | 151–152°d | 69.13 | 8.41 | 4.03 | 69.08 | 8.62 | 3.94 |
| 32 | $CH_2Ph$ | H | F | 142–143° | 69.28 | 7.04 | 4.25 | 69.06 | 6.93 | 4.19 |
| 33 | $CH_2C_6H_4F$-4 | H | F | 144–145° | 65.69 | 6.38 | 4.03 | 65.76 | 6.39 | 3.96 |
| 34 | $CH_2C_6H_4F_2$-3,4 | H | F | 142–143° | 62.46 | 5.79 | 3.83 | 62.69 | 5.87 | 3.73 |
| 35 | $CH_2C_6H_4Cl$-4 | H | F | 129–130° | 62.72 | 6.09 | 3.85 | 62.71 | 6.02 | 3.71 |
| 36 | $CH_2C_6H_3Cl_2$-3,4 | H | F | 122–126° | a | | | | | |
| 37 | $CH_2C_6H_4CF_3$-3 | H | F | 160–161° | 60.45 | 5.58 | 3.52 | 60.26 | 5.49 | 3.39 |
| 38 | $CH_2C_6H_4CF_3$-4 | H | F | 152–153° | 60.45 | 5.58 | 3.52 | 60.54 | 5.53 | 3.45 |

TABLE II-continued

Structure: R² at position 4/5, cyclohexene ring fused to cyclopentane with NR¹R² at position 1,2 (cis), positions 3a, 7a ring junction.

| Example No. | R¹ | R² | F = fum. H = HCl | m.p. | C calcd. | H calcd. | N calcd. | C found | H found | N found |
|---|---|---|---|---|---|---|---|---|---|---|
| 39 | CH₂-furan (2-furyl) | H | F | 107–108° | 63.94 | 6.63 | 4.39 | 63.99 | 6.62 | 4.25 |
| 40 | CH₂-thiophene (2-thienyl) | H | H | 196–197° | 61.04 | 7.09 | 5.48 | 60.88 | 6.96 | 5.43 |
| 41 | CH₂CH₂Ph | H | F | 126–127° | 69.95 | 7.34 | 4.08 | 70.01 | 7.23 | 4.01 |
| 42 | CH₂CH₂C₆H₄F-2 | H | H | 171–173° | 68.20 | 7.51 | 4.97 | 68.42 | 7.47 | 4.83 |
| 43 | CH₂CH₂C₆H₄F-3 | H | H | 197–199°d | 68.20 | 7.51 | 4.97 | 68.30 | 7.35 | 4.85 |
| 44 | CH₂CH₂C₆H₃F₂-3,4 | H | H | 192–193° | 64.10 | 6.72 | 4.67 | 63.90 | 6.63 | 4.51 |
| 45 | CH₂CH₂C₆H₃F₂-3,5 | H | H | 224–226°d | 64.10 | 6.72 | 4.67 | 64.23 | 6.76 | 4.49 |
| 46 | CH₂CH₂C₆H₄Cl-3 | H | H | 188–189° | b | | | | | |
| 47 | CH₂CH₂C₆H₄Cl-4 | H | F | 154–155° | c | | | | | |
| 48 | CH₂CH₂C₆H₄CF₃-4 | H | F | 126–127° | 61.31 | 5.88 | 3.40 | 61.58 | 5.87 | 3.36 |
| 49 | CH₂CH₂C₆H₄CF₃-4 | H | F | 137–138° | 61.31 | 5.88 | 3.40 | 60.86 | 5.78 | 3.25 |
| 50 | CH₂CH₂C₆H₄NO₂-4 | H | F | 161–162° | 61.85 | 6.23 | 7.21 | 61.85 | 6.22 | 7.06 |
| 51 | CH₂CH₂C₆H₄OMe-4 | H | F | 138–139° | 67.54 | 7.29 | 3.75 | 67.22 | 7.24 | 3.67 |
| 52 | CH₂CH₂C₆H₄OH-4 | H | H | 201–203° | 68.68 | 7.93 | 5.01 | 68.81 | 7.94 | 4.91 |
| 53 | CH₂CH₂Ph | 3aMe | F | 177–178° | 70.56 | 7.61 | 3.92 | 70.70 | 7.62 | 3.83 |
| 54 | CH₂CH₂C₆H₄F-4 | 5-Me | H | 180°d | 69.02 | 7.84 | 4.74 | 68.94 | 7.89 | 4.53 |
| 55 | CH₂CH₂Ph | 5-Ph | H | 177–181° | d | | | | | |
| 56 | CH₂CH₂Ph | 4,7-Ph₂ | H | 185–187° | 80.84 | 7.27 | 3.37 | 80.66 | 7.33 | 3.19 |
| 57 | cyclopropyl-C₆H₅ (CH with cyclopropane and phenyl) | H | F | 136–138°d | 70.96 | 7.09 | 3.94 | 70.89 | 7.00 | 3.85 |
| 58 | CH₂CHPh₂ | H | F | 171–172°d | 74.44 | 6.97 | 3.34 | 74.40 | 6.90 | 3.27 |
| 59 | (CH₂)₂-1-naphthyl | H | F | 146–147° | 73.26 | 6.92 | 3.56 | 72.93 | 6.84 | 3.46 |
| 60 | (CH₂)₂-2-thienyl | H | F | 132–133° | 61.87 | 6.63 | 4.01 | 61.93 | 6.56 | 4.01 |
| 61 | (CH₂)₂-3-thienyl | H | F | 129–130° | 61.87 | 6.63 | 4.01 | 61.68 | 6.59 | 4.01 |
| 62 | (CH₂)₂-3-indolyl | H | H | 201–202° | 71.38 | 7.66 | 9.25 | 7.18 | 7.79 | 9.07 |
| 63 | (CH₂)₂Ph | 4,7-Me₂; 5-(CH₂)₄-6 | F | 208–210°d | 73.38 | 8.29 | 3.29 | 72.92 | 8.40 | 3.46 |
| 64 | (CH₂)₃Ph | H | F | 141–142° | 70.56 | 7.61 | 3.92 | 70.58 | 7.56 | 3.88 |
| 65 | CH₂CH₂CHPh₂ | H | F | 163–164° | 74.80 | 7.21 | 3.23 | 74.90 | 7.12 | 3.18 | a ¹H NMR spectrum of the free base (in CDCl₃): δ 7.4(s, 1H); 7.4(d, 1H); 7.2(d, 1H); 5.8(m, 2H); 3.6(s, 2H); 2 2.1–2.3(m, 4H) and 1.9(d, 2H).
b ¹H NMR spectrum of the free base (in CDCl₃): δ 7.2(m, 3H); 7.1(d, split further, 1H); 5.8(m, 2H); 3.0(m, 2H); (m, 4H); 2.4(m, 2H); 2.1–2.3(m, 4H) and 1.9(d, 2H).
c ¹H NMR spectrum of the free base (in CDCl₃): δ 7.2(d, 2H); 7.1(d, 2H); 5.8(m, 2H); 3.0(m, 2H); 2.6–2.8(m, 4H) 1.9(d, 2H).
b High-resolution mass spectrum of free base: calcd. for C₂₂H₂₅N: 303. 1987; measured: 303. 1988.

Tables III and IV contain examples of additional compounds which may be prepared by the methods disclosed above.

TABLE III

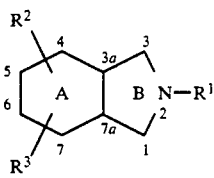

| Ex. # | R¹ | R² | R³ | Ring A Double Bond Position |
|---|---|---|---|---|
| 66 | 4-CH₃C₆H₄CH₂CH₂ | 5-Ph | H | — |
| 67 | 3-t-BuC₆H₄CH₂ | 4-Ph | H | — |
| 68 | 4-cyclohexylC₆H₄CH₂CH₂ | H | H | — |
| 69 | 4-H₂C=CHCH₂C₆H₄CH₂ | 5=O | 3a-CH₃ | 5, 6 |
| 70 | 4-n-C₄F₉C₆H₄CH₂ | H | H | 5, 6 |
| 71 | 4-CF₃C₆H₄CH₂ | 5=O | 6-CH₃ | 5, 6 |
| 72 | 4-CF₃C₆H₄CH₂ | 4-CH₃ | 7-CH₃ | 5, 6 |
| 73 | 4-CF₃C₆H₄CH₂ | H | H | 4, 5 |
| 74 | 4-CF₃C₆H₄CH₂ | H | H | 3a, 4 |
| 75 | 4-CF₃C₆H₄CH₂ | H | H | 3a, 7a |
| 76 | 4-C₂F₅C₆H₄CH₂ | H | H | 5, 6 |
| 77 | 4-C₂F₅C₆H₄CH₂ | H | H | 5, 6 |
| 78 | 3-CH₃SOC₆H₄CH₂CH₂ | 5-OH | H | — |
| 79 | 4-C₂H₅SO₂C₆H₄CH₂ | 6-CH₃CO | 4-cyclopropyl | — |
| 80 | 2-C₂H₅SC₆H₄CH₂CH₂ | H | H | 5, 6 |
| 81 | 4-H₂NC₆H₄CH₂CH₂ | Cl | H | 5, 6 |
| 82 | 4-CH₃NHC₆H₄CH₂ | H | H | 5, 6 |
| 83 | 4-(CH₃)₂NC₆H₄CH₂CH₂ | H | H | 5, 6 |
| 84 | 4-NC₆H₄CH₂ | H | H | — |
| 85 | 3-HO₂CC₆H₄CH₂CH₂ | H | H | — |
| 86 | 4-C₂H₅O₂C₆H₄(CH₂)₃ | H | H | 5, 6 |
| 87 | 3-benzofurylethyl | H | H | 5, 6 |
| 88 | 2-pyrrolylmethyl | 4-furyl | H | — |
| 89 | 4-quinolylpropyl | H | H | 5, 6 |
| 90 | 2-isoquinolylmethyl | 5-(3-indolyl) | H | — |
| 91 | 2-benzothienylthyl | H | H | 5, 6 |
| 92 | 2-pyrimidylethyl | H | H | 5, 6 |
| 93 | 2-pyrazinylpropyl | H | H | 5, 6 |
| 94 | 2-quinazolylethyl | H | H | 5, 6 |
| 95 | 2-phthalazinylbutyl | H | H | 5, 6 |
| 96 | 2-naphthyridinyl | H | H | — |
| 97 | 4-CF₃C₆H₄CH₂ | 4-(CH₂CH₂CH₂CH₂)-5 | — | — |
| 98 | 4-ClC₆H₄CH₂CH₂ | 3a-(CH₂CH₂CH₂)-4 | — | — |
| 99 | 4-ClC₆H₄CH₂CH₂ | 5-CH₂CH(CH₃)CH₂CH₂-6 | — | — |
| 100 | 4-CF₃C₆H₄CH₂ | 4=O | H | 5, 6 |
| 101 | 4-CF₃-3ClC₆H₃CH₂ | H | H | 5, 6 |
| 102 | 4-Cl-3-CF₃C₆H₃CH₂CH₂ | H | H | — |
| 103 | 4-ClC₆H₄(CH₂)₅ | H | H | — |
| 104 | C₆H₅(CH₂)₆ | H | H | 5, 6 |

TABLE IV

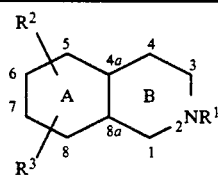

| Ex. # | R¹ | R² | R³ | Ring A Double Bond Position |
|---|---|---|---|---|
| 105 | CF₃C₆H₄(CH₂)₃ | H | H | — |
| 106 | 4-ClC₆H₄CH₂CH₂ | H | H | — |
| 107 | C₆H₅(CH₂)₃ | 4a-CH₃ | H | — |
| 108 | 4-CF₃C₆H₄CH₂ | 6=O | H | 4a, 5 |
| 109 | 4-CF₃C₆H₄CH₂ | H | H | 5, 6 |
| 110 | 4-ClC₆H₄CH₂CH₂ | H | H | 6, 7 |
| 111 | 4-CF₃C₆H₄CH₂ | H | H | 7, 8 |
| 112 | 4-ClC₆H₄CH₂ | H | H | 8, 8a |
| 113 | 4-CF₃C₆H₄CH₂ | H | H | 4a, 8a |
| 114 | cyclohexyl | H | H | — |

TABLE IV-continued

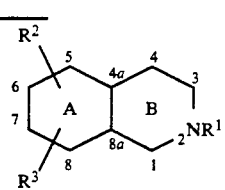

| Ex. # | R¹ | R² | R³ | Ring A Double Bond Position |
|---|---|---|---|---|
| 115 | cyclooctylmethyl | H | H | — |

UTILITY SECTION

The compounds of this invention and their pharmaceutically acceptable salts possess psychotropic properties, particularly antipsychotic activity of good duration with potent sigma receptor antagonist activities while lacking the typical movement disorder side-effects of standard dopamine receptor antagonist antipsychotic agents. These compounds may also be useful as antidotes for certain psychotomimetic agents such as phencyclidine (PCP), and as antidyskinetic agents.

In Vitro

Sigma Receptor Binding Assay

Male Hartley guinea pigs (250-300 g, Charles River) were sacrificed by decapitation. Brain membranes were prepared by the method of Tam (Proc. Natl. Acad. Sci. USA 80: 6703-6707, 1983). Whole brains were homogenized (20 seconds) in 10 vol (wt/vol) of ice-cold 0.34 M sucrose with a Brinkmann Polytron (setting 8). The homogenate was centrifuged at 920×g for 10 minutes. The supernatant was centrifuged at 47,000 ×g for 20 minutes. The resulting membrane pellet was resuspended in 10 vol (original wt/vol) of 50 mM Tris HCl (pH 7.4) and incubated at 37° C. for 45 minutes to degrade and dissociate bound endogenous ligands. The membranes were then centrifuged at 47,000×g for 20 minutes and resuspended in 50 mM Tris HCl (50 mL per brain).

0.5 mL aliquots of the membrane preparation were incubated with unlabeled drugs, 1 nM (+)-[$^3$H]SKF 10,047 in 50 mM Tris HCl, pH 7.4, in a final volume of 1 mL. Nonspecific binding was measured in the presence of 10 μM (+)-SKF 10,047. The apparent dissociation constant (Kd) for (+)-[$^3$H]SKF 10,047 is 50 nM. After 45 minutes of incubation at room temperature, samples were filtered rapidly through Whatman GF/C glass filters under negative pressure, and washed 3 times with ice-cold Tris buffer (5 mL).

IC$_{50}$s were calculated from log-logit plots. Apparent K$_i$s were calculated from the equation, K$_i$ = IC$_{50}$/[1+(L/Kd)](4), where L is the concentration of radioligand and K$_d$ is its dissociation constant. The data are shown in Table V under the heading SIGMA.

Dopamine Receptor Binding

Membranes were prepared from guinea pig striatum by the method described for sigma receptor binding. The membranes were then resuspended in 50 mM Tris HCl (9 mL per brain).

0.5 mL aliquots of the membrane preparation were incubated with unlabeled drugs, and 0.15 nM [$^3$H]spiperone in a final volume of 1 mL containing 50 mM Tris HCl, 120 mM NaCl and 1 mM MgCl$_2$ (pH 7.7). Nonspecific binding was measured in the presence of 100 nM (+)-butaclamol. After 15 minutes of incubation at 37° C., samples were filtered rapidly through Whatman GF/C glass filters under negative pressure, and washed three times with ice-cold binding buffer (5 mL).

IC$_{50}$s were calculated from log-logit plots. Apparent K$_i$s were calculated from the equation K$_i$ = IC$_{50}$[1+(L/K$_d$)](4), where L is the concentration of radioligand and K$_d$ is its dissociation constant. The data are shown in Table V under the heading DRB.

The examples of this invention exhibit potent binding affinity for sigma receptors but not for dopamine receptors. Therefore these compounds are not expected to produce the extrapyramidal symptoms that are typical of that produced by haloperidol and other typical antipsychotics that are dopamine receptor antagonists.

In Vivo

Mescaline-Induced Scratching in Mice

This is a modification of the procedure of Fellows and Cook (in Psychotropic Drugs, ed. by S. Garrattini and V. Ghatti, pp. 397-404, Elsevier, Amsterdam, 1957) and Deegan and Cook (J. Pharmacol. Exp. Ther. 122: 17A, 1958). Male CF1 Mice (Charles River) were injected orally with test compound and placed singly into square (13 cm) Plexiglass observation chambers. Twenty minutes later mice were injected orally with mescaline (25 mg/kg). Beginning 25 minutes after treatment with mescaline (45 minutes after treatment with test compound), scratching episodes were counted during a 5 minute observation period. A scratching episode is defined as a brief (1-2 sec) burst of scratching either the head or the ear with the hind foot. The data are shown in Table V under the heading MUR MESC.

Isolation-Induced Aggression in Mice

This is a modification of the method of Yen et al. (Arch. Int. Pharmacodyn. 123: 179-185, 1959) and Jannsen et al. (J. Pharmacol. Exp. Ther. 129: 471-475, 1960). Male Balb/c mice (Charles River) were used. After 2-4 weeks of isolation in plastic cages (11.5×5.75×6 in) the mice were selected for aggression by placing a normal group-housed mouse in the cage with the isolate for a maximum of 3 minutes. Isolated mice failing to consistently attack an intruder were removed from the colony.

Drug testing was carried out by treating the isolated mice with test drugs or standards. Thirty minutes after dosing with test drugs by the oral route, one isolated mouse was removed from its home cage and placed in the home cage of another isolate. Scoring was a yes or no response for each pair. A maximum of 3 minutes was allowed for an attack and the pair was separated immediately upon an attack. Selection of home cage and intruder mice was randomized for each test. Mice were treated and tested once or twice a week with at least a 2 day washout period between treatments. The data are shown in . . . under the heading MUR MIIA.

TABLE V

| Example No. | SIGMA | DRB | MUR MESC | MUR MIIA |
|---|---|---|---|---|
| 1 | +++ | − | +++ | |
| 2 | +++ | − | +++ | |
| 3 | +++ | − | +++ | |
| 4 | +++ | − | | |
| 5 | + | − | +++ | |
| 6 | +++ | − | +++ | |
| 7 | +++ | − | + | |
| 8 | +++ | − | +++ | |
| 9 | +++ | − | | |
| 10 | +++ | − | +++ | |
| 11 | +++ | − | ++ | |
| 12 | +++ | + | | |
| 13 | +++ | − | | |
| 14 | +++ | − | | |
| 14a | +++ | − | | |
| 14b | +++ | − | ++ | |
| 15 | +++ | − | | |
| 16 | +++ | − | | |
| 17 | +++ | − | +++ | |
| 18 | +++ | − | | |
| 19 | +++ | − | +++ | − |
| 20 | +++ | − | ++ | |
| 21 | +++ | − | +++ | + |
| 22 | +++ | − | | |
| 23 | +++ | − | | |
| 24 | +++ | − | + | |
| 25 | + | − | | |
| 26 | + | − | | |
| 27 | +++ | − | | |
| 28 | +++ | − | | |
| 29 | +++ | − | | |
| 30 | +++ | − | | |
| 31 | +++ | − | | |
| 32 | +++ | − | | |
| 33 | +++ | − | | |

TABLE V-continued

| Example No. | SIGMA | DRB | MUR MESC | MUR MIIA |
|---|---|---|---|---|
| 34 | +++ | − | | |
| 35 | +++ | − | | |
| 36 | +++ | − | + | |
| 37 | +++ | − | + | |
| 38 | +++ | − | ++ | ++ |
| 39 | +++ | − | | |
| 40 | +++ | − | +++ | |
| 41 | +++ | − | +++ | |
| 42 | +++ | − | | |
| 43 | +++ | − | | |
| 44 | +++ | − | | |
| 45 | +++ | − | | |
| 46 | +++ | − | | |
| 47 | +++ | − | +++ | |
| 48 | +++ | − | + | |
| 49 | +++ | − | + | |
| 50 | +++ | − | + | + |
| 51 | +++ | − | | |
| 52 | +++ | − | | |
| 53 | +++ | − | | |
| 54 | +++ | − | +++ | |
| 55 | +++ | ++ | +++ | |
| 56 | +++ | − | | |
| 57 | +++ | − | | |
| 58 | + | − | | |
| 59 | +++ | − | | |
| 60 | +++ | − | | |
| 61 | +++ | − | | |
| 62 | +++ | − | | |
| 63 | +++ | − | +++ | |
| 64 | +++ | − | | |
| 65 | +++ | − | + | |

Dosage Forms

Daily dosage ranges from 1 mg to 2000 mg. Dosage forms (compositions) suitable for administration ordinarily will contain 0.5–95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

What is claimed is:

1. A compound having the formula:

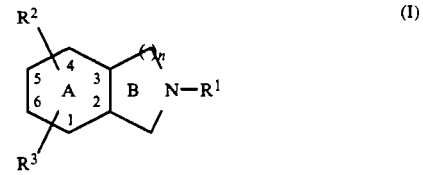

(I)

or a pharmaceutically acceptable salt, N-oxide, chiral, enantiomeric, diastereomeric or racemic form thereof, wherein:

$n = 1$;

$R^1$ is selected from the group:
  $C_1$–$C_8$ alkyl substituted with 1 or more $R^4$, $C_3$–$C_8$ cycloalkyl, and $C_4$–$C_{10}$ cycloalkyl-alkyl;

$R^2$ and $R^3$ are optional and are independently selected from the group:
  $C_1$–$C_8$ alkyl substituted with 0–3 $R^4$, $C_2$–$C_8$ alkenyl, $C_3$–$C_8$ cycloalkyl, $C_4$–$C_{10}$ cycloalkyl-alkyl $C_1$–$C_6$ perfluoroalkyl,
  aryl optionally substituted with 1–3 of the following:
    $C_1$–$C_8$ alkyl, $C_2$–$C_8$ alkenyl, $C_3$–$C_8$ cycloalkyl, $C_1$–$C_6$ perfluoroalkyl, aryl, —F, —Cl, —Br, —I, —$NO_2$, —$OR^5$, —OC(=O)$R^7$, —N($R^7$)$_2$, —$SR^5$, —S(O)$R^5$, —$SO_2R^5$, —$CO_2R^7$, —CN,
  except that $R^2$ and/or $R^3$ when aryl may not be at the 2- or 3-position,
  —F, —Cl, —Br, —I, —$NO_2$, —$OR^5$, —OC(=O)$R^7$, —N($R^7$)$_2$, —$SR^5$, —S(O)$R^5$, —$SO_2R^5$, —$CO_2R^7$, $COR^7$, —CN,
  or =O, forming a carbonyl group;

$R^4$ is aryl optionally substituted with 1–3 of the following:
  $C_1$–$C_8$ alkyl, $C_2$–$C_8$ alkenyl, $C_3$–$C_8$ cycloalkyl, $C_1$–$C_6$ perfluoroalkyl, aryl, —F, —Cl, —Br, —I, —$NO_2$, —$OR^5$, —OC(=O)$R^7$, —N($R^7$)$_2$, —$SR^5$, —S(O)$R^5$, —$SO_2R^5$, —$CO_2R^7$, —CN;

$R^5$ is independently selected at each occurrence from the group:
  hydrogen, $C_1$–$C_{14}$ alkyl, $C_3$–$C_8$ cycloalkyl, $C_1$–$C_6$ alkanoyl, and aryl;

$R^7$ is H, phenyl, benzyl or $C_1$–$C_6$ alkyl;

the A ring may contain one double bond;

with the following provisos:
  (1) when $R^2$ and $R^3$ are on the same atom, neither $R^2$ nor $R^3$ are OH;
  (2) when $n = 1$ and $R^2$ is 5-hydroxy and $R^3$ is 6-alkoxy and the A ring contains no double bond, then $R^1$ cannot be —$CH_2CH_2$Ph or —$CH_2CH_2$-(naphthyl);
  (3) when $n = 1$ and $R^2$ is 5-hydroxy or 5-acyloxy and $R^3$ is alkoxy and the A ring contains no double bond, then $R^1$ cannot be —(CH$_2$)$_p$aryl wherein $p = 1$–3 and the aryl groups are substituted with 1–3 $R^7$;
  (4) when $n = 1$ and $R^2$ is not present and $R^3$ is not present and the A ring contains a double bond between carbons 5 and 6, then $R^1$ cannot be —$CH_2$Ph;

(5) when n=1 and $R^2$ is 5-Cl and $R^3$ is not present and the A ring contains a double bond between carbons 5 and 6, then $R^1$ cannot be —CH$_2$Ph; then $R^1$ cannot be —CH$_2$Ph;

(6) when n=1 and $R^2$ is 5-OH and $R^3$ is not present and the A ring contains no double bond, then $R^1$ cannot be —CH$_2$Ph;

(7) when n=1 and $R^2$ is 5-keto or 5-[1-(1,3-dioxolane)] and $R^3$ is not present and the A ring contains no double bond, then $R^1$ cannot be —CH$_2$Ph;

(8) when n=1 and $R^2$ is not present and $R^3$ is not present and the A ring contains no double bond, then $R^1$ cannot be —CH$_2$(2-methylcyclohexyl);

(9) when n=1 and $R^2$ is 5-Ph and $R^3$ is not present and the A ring contains no double bond, then $R^1$ cannot be —CH$_2$CH$_2$(3,4-dimethoxyphenyl);

(12) when n=1 and $R^2$ is not present and $R^3$ is not present and the A ring contains no double bond, then $R^1$ cannot be —CH$_2$CHCH$_3$CH$_2$(4-t-butylphenyl).

2. The compound of claim 1 wherein:
n=1;
$R^1$ is $C_1$-$C_6$ alkyl substituted with 1 or more $R^4$ or $C_4$-$C_{10}$ cycloalkylalkyl;
$R^2$ is H, OH or =O;
$R^3$ is H, $C_1$-$C_8$ alkyl substituted with 0-3 $R^4$ or phenyl optionally substituted with 1-3 F, Cl, Br, NO$_2$, CN, $C_1$-$C_8$ alkyl, and aryl, provided that phenyl is not in the 2- or 3-position;
$R^4$ is aryl optionally substituted with 1-3 of the following:
$C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN;
$R^5$ is independently selected at each occurrence from the group:
hydrogen, $C_1$-$C_{14}$ alkyl, $C_3$-$C_8$ cycloalkyl, $C_1$-$C_6$ alkanoyl, and aryl;
$R^7$ is H, phenyl, benzyl or $C_1$-$C_6$ alkyl; and
the A ring may contain one double bond; with the following provisos:

(1) when n=1 and $R^2$ is not present and $R^3$ is not present and the A ring contains a double bond between carbons 5 and 6, then $R^1$ cannot be —CH$_2$Ph;

(2) when n=1 and $R^2$ is 5-OH and $R^3$ is not present and the A ring contains no double bond, then $R^1$ cannot be —CH$_2$Ph;

(3) when n=1 and $R^2$ is 5-keto and $R^3$ is not present and the A ring contains no double bond, then $R^1$ cannot be —CH$_2$Ph;

(5) when n=1 and $R^2$ is not present and $R^3$ is not present and the A ring contains no double bond, then $R^1$ cannot be —CH$_2$CHCH$_3$CH$_2$(4-t-butylphenyl).

3. The compound of claim 1 wherein:
n=1;
$R^1$ is $C_1$-$C_6$ alkyl substituted with 1 $R^4$ wherein 1-3 carbon atoms separate N from $R^4$;
$R^2$ is H, OH or =O;
$R^3$ is H or $C_1$-$C_8$ alkyl;
$R^4$ is aryl optionally substituted with 1-3 of the following:
$C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN;
$R^5$ is independently selected at each occurrence from the group:
hydrogen, $C_1$-$C_{14}$ alkyl, $C_3$-$C_8$ cycloalkyl, $C_1$-$C_6$ alkanoyl, and aryl;
$R^7$ is H, phenyl, benzyl or $C_1$-$C_6$ alkyl; and
the A ring may contain one double bond; with the following provisos:

(1) when n=1 and $R^2$ is not present and $R^3$ is not present and the A ring contains a double bond between carbons 5 and 6, then $R^1$ cannot be —CH$_2$Ph;

(2) when n=1 and $R^2$ is 5-OH and $R^3$ is not present and the A ring contains no double bond, then $R^1$ cannot be —CH$_2$Ph;

(3) when n=1 and $R^2$ is 5-keto and $R^3$ is not present and the A ring contains no double bond, then $R^1$ cannot be —CH$_2$Ph;

(5) when n=1 and $R^2$ is not present and $R^3$ is not present and the A ring contains no double bond, then $R^1$ cannot be —CH$_2$CHCH$_3$CH$_2$(4-t-butylphenyl).

4. The compound of claim 1 wherein:
n=1;
$R^1$ is $C_1$-$C_6$ alkyl substituted with 1 $R^4$ wherein 1-3 carbon atoms separate N from $R^4$;
$R^2$ is H;
$R^3$ is H or $C_1$-$C_8$ alkyl;
$R^4$ is aryl optionally substituted with 1-3 of the following:
$C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN;
$R^5$ is independently selected at each occurrence from the group:
hydrogen, $C_1$-$C_{14}$ alkyl, $C_3$-$C_8$ cycloalkyl, $C_1$-$C_6$ alkanoyl, and aryl;
$R^7$ is H, phenyl, benzyl or $C_1$-$C_6$ alkyl; and
the A ring may contain one double bond; with the following provisos:

(1) when n=1 and $R^2$ is not present and $R^3$ is not present and the A ring contains a double bond between carbons 5 and 6, then $R^1$ cannot be —CH$_2$Ph;

(2) when n=1 and $R^2$ is 5-OH and $R^3$ is not present and the A ring contains no double bond, then $R^1$ cannot be —CH$_2$Ph;

(3) when n=1 and $R^2$ is 5-keto and $R^3$ is not present and the A ring contains no double bond, then $R^1$ cannot be —CH$_2$Ph;

(5) when n=1 and $R^2$ is not present and $R^3$ is not present and the A ring contains no double bond, then $R^1$ cannot be —CH$_2$CHCH$_3$CH$_2$(4-t-butylphenyl).

5. The compound of claim 1 which is cis-2-(4-trifluoromethylbenzyl)-3a, 4,7,7a-tetrahydroisoindoline.

6. The compound of claim 1 which is cis-4-chlorophenethylhexahydroisoindole;

7. The compound of claim 1 which is trans-2-phenethylhexahydroisoindoline;

8. The compound of claim 1 which is cis-2-phenethylhexahydroisoindoline.

9. A pharmaceutical composition comprising a pharmaceutically acceptable carrier and an antipsychotic effective amount of a compound of claim 1.

10. A pharmaceutical composition comprising a pharmaceutically acceptable carrier and an antipsychotic effective amount of a compound of claim 2.

11. A pharmaceutical composition comprising a pharmaceutically acceptable carrier and an antipsychotic effective amount of a compound of claim 3.

12. A pharmaceutical composition comprising a pharmaceutically acceptable carrier and an antipsychotic effective amount of a compound of claim 4.

13. A pharmaceutical composition comprising a pharmaceutically acceptable carrier and an antipsychotic effective amount of a compound of claim 5.

14. A pharmaceutical composition comprising a pharmaceutically acceptable carrier and an antipsychotic effective amount of a compound of claim 6.

15. A pharmaceutical composition comprising a pharmaceutically acceptable carrier and an antipsychotic effective amount of a compound of claim 7.

16. A pharmaceutical composition comprising a pharmaceutically acceptable carrier and an antipsychotic effective amount of a compound of claim 8.

17. A pharmaceutical composition comprising a pharmaceutically acceptable carrier and an antipsychotic effective amount of a compound of claim 9.

18. A method for treatment of physiological or drug induced psychosis or dyskinesia in a mammal comprising administering to a mammal in need of such treatment an antipsychotic or antidyskinetic effective amount of a compound of formula:

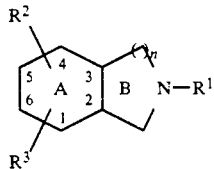

(I)

or a pharmaceutically acceptable salt, N-oxide, chiral, enantiomeric, diastereomeric or racemic form thereof, wherein:

$n = 1$;

$R^1$ is selected from the group:
 $C_1$-$C_6$ alkyl substituted with 1 or more $R^4$, $C_3$-$C_8$ cycloalkyl, and $C_4$-$C_{10}$ cycloalkyl-alkyl;

$R^2$ and $R^3$ are optional and are independently selected from the group:
 $C_1$-$C_8$ alkyl substituted with 0-3 $R^4$, $C_2$-$C_8$ alkenyl, $C_3$-$C_8$ cycloalkyl, $C_4$-$C_{10}$ cycloalkyl-alkyl, $C_1$-$C_6$ perfluoroalkyl,
 aryl optionally substituted with 1-3 of the following:
  $C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN,
 except that $R^2$ and/or $R^3$ when aryl may not be at the 2- or 3-position,
 —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, COR$^7$, —CN,
 or =O, forming a carbonyl group;

$R^4$ is aryl optionally substituted with 1-3 of the following:
 $C_1$-$C_8$ alkyl, $C_2$-$C_8$ alkenyl, $C_3$-$C_8$ cycloalkyl, $C_1$-$C_6$ perfluoroalkyl, aryl, —F, —Cl, —Br, —I, —NO$_2$, —OR$^5$, —OC(=O)R$^7$, —N(R$^7$)$_2$, —SR$^5$, —S(O)R$^5$, —SO$_2$R$^5$, —CO$_2$R$^7$, —CN;

$R^5$ is independently selected at each occurrence from the group:
 hydrogen, $C_1$-$C_{14}$ alkyl, $C_3$-$C_8$ cycloalkyl, $C_1$-$C_6$ alkanoyl, and aryl;

$R^7$ is H, phenyl, benzyl or $C_1$-$C_6$ alkyl;

the A ring may contain one double bond;

with the following provisos:
 (1) when $R^2$ and $R^3$ are on the same atom, neither $R^2$ nor $R^3$ are OH;
 (2) when $n = 1$ and $R^2$ is 5-hydroxy and $R^3$ is 6-alkoxy and the A ring contains no double bond, then $R^1$ cannot be —CH$_2$CH$_2$Ph or —CH$_2$CH$_2$(naphthyl);
 (3) when $n = 1$ and $R^2$ is 5-hydroxy or 5-acyloxy and $R^3$ is alkoxy and the A ring contains no double bond, then $R^1$ cannot be —(CH$_2$)$_p$aryl wherein $p = 1$-3 and the aryl is substituted with 1-3 $R^7$.

19. A method for treatment of physiological or drug induced psychosis or dyskinesia in a mammal comprising administering to a mammal in need of such treatment an antipsychotic or antidyskinetic effective amount of a compound of claim 2.

20. A method for treatment of physiological or drug induced psychosis or dyskinesia in a mammal comprising administering to a mammal in need of such treatment an antipsychotic or antidyskinetic effective amount of a compound of claim 3.

21. A method for treatment of physiological or drug induced psychosis or dyskinesia in a mammal comprising administering to a mammal in need of such treatment an antipsychotic or antidyskinetic effective amount of a compound of claim 4.

22. A method for treatment of physiological or drug induced psychosis or dyskinesia in a mammal comprising administering to a mammal in need of such treatment an antipsychotic or antidyskinetic effective amount of a compound of claim 5.

23. A method for treatment of physiological or drug induced psychosis or dyskinesia in a mammal comprising administering to a mammal in need of such treatment an antipsychotic or antidyskinetic effective amount of a compound of claim 6.

24. A method for treatment of physiological or drug induced psychosis or dyskinesia in a mammal comprising administering to a mammal in need of such treatment an antipsychotic or antidyskinetic effective amount of a compound of claim 7.

25. A method for treatment of physiological or drug induced psychosis or dyskinesia in a mammal comprising administering to a mammal in need of such treatment an antipsychotic or antidyskinetic effective amount of a compound of claim 8.

26. A method for treatment of physiological or drug induced psychosis or dyskinesia in a mammal comprising administering to a mammal in need of such treatment an antipsychotic or antidyskinetic effective amount of a compound of claim 9.

* * * * *